United States Patent
Shewmaker

(10) Patent No.: US 6,972,351 B2
(45) Date of Patent: Dec. 6, 2005

(54) METHODS FOR PRODUCING CAROTENOID COMPOUNDS AND SPECIALTY OILS IN PLANT SEEDS

(75) Inventor: Christine K. Shewmaker, Woodland, CA (US)

(73) Assignee: Calgene LLC, Davis, CA (US)

( * ) Notice: Subject to any disclaimer, the term of this patent is extended or adjusted under 35 U.S.C. 154(b) by 389 days.

(21) Appl. No.: 10/041,472

(22) Filed: Jan. 10, 2002

(65) Prior Publication Data

US 2002/0092039 A1 Jul. 11, 2002

Related U.S. Application Data

(63) Continuation of application No. 08/908,758, filed on Aug. 8, 1997, now Pat. No. 6,429,356.
(60) Provisional application No. 60/024,145, filed on Aug. 9, 1996.

(51) Int. Cl.[7] .................. C12N 15/31; C12N 15/52; C12N 15/82; A01H 5/00; A01H 5/10
(52) U.S. Cl. .................. 800/306; 800/278; 800/282; 800/287; 800/288; 800/298; 536/23.1; 536/23.2; 536/23.7
(58) Field of Search ................ 800/278, 281, 800/287, 298, 306, 312, 320, 326, 282, 288; 536/23.6, 23.7, 23.1, 23.2

(56) References Cited

U.S. PATENT DOCUMENTS

| | | | |
|---|---|---|---|
| 4,727,219 A | | 2/1988 | Brar et al. |
| 5,304,478 A | | 4/1994 | Bird et al. |
| 5,429,939 A | | 7/1995 | Misawa et al. |
| 5,432,069 A | | 7/1995 | Grüninger et al. |
| 5,618,988 A | | 4/1997 | Hauptmann et al. |
| 5,684,238 A | | 11/1997 | Ausich et al. |
| 5,750,865 A | | 5/1998 | Bird et al. |
| 5,792,903 A | | 8/1998 | Hirschberg et al. |
| 6,429,356 B1 | * | 8/2002 | Shewmaker ........... 800/278 |
| 6,653,530 B1 | * | 11/2003 | Shewmaker et al. ...... 800/282 |
| 2002/0092039 A1 | | 7/2002 | Shewmaker et al. |

FOREIGN PATENT DOCUMENTS

| | | |
|---|---|---|
| WO | 91/02059 | 2/1991 |
| WO | 91/09128 | 6/1991 |
| WO | 91/13078 | 9/1991 |
| WO | 93/18158 | 9/1993 |
| WO | 94/11516 | 5/1994 |
| WO | 94/12014 | 6/1994 |
| WO | 94/18337 | 8/1994 |
| WO | 95/06128 A3 | 3/1995 |
| WO | 95/06128 A2 | 3/1995 |
| WO | 95/08914 | 4/1995 |
| WO | 95/18220 | 7/1995 |
| WO | 95/23863 | 9/1995 |
| WO | 95/34668 | 12/1995 |
| WO | 96/02650 A2 | 2/1996 |
| WO | 96/02650 A3 | 2/1996 |
| WO | 96/06172 | 2/1996 |
| WO | 96/13149 | 5/1996 |
| WO | 96/13159 | 5/1996 |
| WO | 96/36717 A3 | 11/1996 |
| WO | 96/36717 A2 | 11/1996 |
| WO | 97/17447 | 5/1997 |
| WO | 97/27285 | 7/1997 |
| WO | 98/06862 | 2/1998 |
| WO | 98/18910 | 5/1998 |
| WO | 99/07867 | 2/1999 |
| WO | 99/55889 | 11/1999 |
| WO | 01/088169 | 11/2001 |

OTHER PUBLICATIONS

Ohlrogge J. et al. Biochemical Society Transactions, 2000: vol. 28, part 6, pp. 567–573.*
Misawa et al. J. of Bacteriology, Dec. 1990; p. 6704–6712.*
Sandmann G, et al. FEMS Microbiology Letters 90;1992, pp. 253–258.*
Armstrong G. et al. PNAS, Dec. 1990; vol. 87 pp. 9975–9979.*
Armstrong G. et al. The Journal of Biological Chemistry May 15, 1990, vol. 265, No. 14, pp. 8329–8338.*
Sandmann G, et al. FEMS Microbiology Letters, 1992, vol. 90, pp. 253–258.*
Ohlrogge J. et al. Biochemical Society Transactions, 2000; vol. 28, part 6, pp. 567–573.*
Burkhardt P. et al. The Plant Journal, 1997, vol. 11; No. 1, pp. 1071–1078.*
Lodato P. et al., Applied and Environmental Microbiology, Aug. 2003; vol. 69, No. 8; pp. 4676–4682.*
Velayos A. et al., Eur. J. Biochem. 2000, vol. 267; pp. 5509–5519.*
Burkhardt P.K. et al. in Rice Genetics III; Proceedings of the Third International Rice Genetics Symposium; Khush G.S. Ed. 1996 (IRRI) International Rice Research Institute.*
Burkhardt P.K. et al. in Experientia Abstract S08–07; The 28th Annual Meeting of the Swiss Societies for Experimental Biology, Switzerland. Mar. 27–29, 1996.*
The Rockefeller Foundation, International Program on Rice Biotechnology; Workshop Report Jun. 10–11, 1993. Potential for Carotenoid Biosynthesis in Rice Endosperm.*
Ye X. et al. Science, Jan. 14, 2000; vol. 287, pp. 303–305.*
H.A. Addlesee, et al., "Cloning, sequencing and functional assignment of the chlorophyll biosyntheses gene," FEBS Letters 389: 126–130 (1996).

(Continued)

*Primary Examiner*—Amy J. Nelson
*Assistant Examiner*—Russell Kallis
(74) *Attorney, Agent, or Firm*—Arnold & Porter LLP; M. Todd Rands

(57) ABSTRACT

Methods are provided for producing plants and seeds having altered carotenoid, fatty acid and tocopherol compositions. The methods find particular use in increasing the carotenoid levels in oilseed plants and in providing desirable high oleic acid seed oils.

29 Claims, 20 Drawing Sheets

OTHER PUBLICATIONS

C. Bayley, et al., "Engineering 2,4–D resistance into cotton," *Theor Appl Genet 83*:645–649 (1992).

R. Bentley, "The Shikimate Pathway—A Metabolic Tree with Many Branches," *Critical Reviews™ in Biochemistry and Molecular Biology 25*(5) 307–384 (1990).

P. Beyer, "Phytoene–forming activities in wild–type and transformed rice endosperm," *IRRN* 21:2–3 (Aug.–Dec. 1996).

P. Bramley, et al., "Biochemical characterization of transgenic tomato plants in which carotenoid synthesis has been inhibited through the expression of antisense RNA to pTOM5," *The Plant Journal 2*(3): 343–349 (1992).

J. Breitenbach, et al., "Expression in *Escherichia coli* and properties of the carotene ketolase from *Haematococcus pluvialis*," *FEMS Microbiology Letters 140*: 241–46 (1996).

B. Buckner, et al., "The yl Gene of Maize Codes for Phytoene Synthase," *Genetics 143*: 479–488 (May 1996).

P. Burkhardt, et al., "Genetic Engineering of Provitamin A Biosynthesis in Rice Endosperm," *Experientia*, S08–07.

P. K. Burkhardt, et al., "Transgenic rice (*Oryza sativa*) endosperm expressing daffodil (*Narcissus pseudonarcissus*) phytoene synthase accumulates phytoene, a key intermediate of provitamin A biosynthesis" *The Plant Journal 11*(5): 1071–1078 (1997).

S. Chaudhuri, et al., "The purification of shikimate dehydrogenase from *Escherichia coli*," *Biochem. J. 226*: 217–223(1985).

T. A. d'Amato, et al., "Subcellular localization of chorismate–mutase isoenzymes in protoplasts from mesophyll and suspension–cultured cells of *Nicotiana silvestris*," *Planta 162*:104–108 (1984).

V. De Luca, "Molecular characterization of secondary metabolic pathways," *AgBiotech News and Information 5*(6): 225N–229N(1993).

A. d'Harlingue, et al., "Plastid Enzymes of Terpenoid Biosynthesis, Purification and Characterization of $_\gamma$–Tocopherol Methyltransferase from *Capsicum* Chromoplasts," *The Journal of Biological Chemistry 260* (28): 15200–15203 (Dec. 5, 1985).

K. Duncan, et al., "The overexpression and complete amino acid sequence of *Excherichia coli* 3–dehydroquinase," *Biochem. J. 238*: 475–483(1986).

M. L. Ericson, et al., "Analysis of the promoter region of napin genes from *Brassica napus* demonstrates binding of nuclear protein in vitro to a conserved sequence motif," *Eur. J. Biochem. 197*: 741–746 (1991).

V. S. Fedenko, et al., Abstract: RU 2005353, Derwent Accession No: 1994–253787.

E. Fiedler, et al., "The formation of homogentisate in the biosynthesis of tocopherol and plastoquinone in spinach chloroplasts," *Planta 155*:511–515 (1982).

P. D. Fraser, et al., "Enzymic confirmation of reactions involved in routes to astaxanthin formation, elucidated using a direct substrate in vitro assay," *Eur. J. Biochem. 252*: 229–236 (1998).

P. D. Fraser, et al., "In Vitro Characterization of Astaxanthin Biosynthetic Enzymes," *The Journal of Biological Chemistry 272*(10) 6128–6135 (Mar. 7, 1997).

R. G. Fray, et al., "Identification and genetic analysis of normal and mutant phytoene synthase genes of tomato by sequencing, complementation and co–suppression," *Plant Molecular Biology* 22: 589–602 (1993).

R. G. Fray, et al., Constitutive expression of a fruit phytoene synthase gene in transgenic tomatoes causes dwarfism by redirecting metabolites from the gibberellin pathway, *The Plant Journal* 8(5): 693–701(1995).

W. C. Fuqua, et al., "Characterization of melA: a gene encoding melanin biosynthesis from the marine bacterium *Shewanella colwelliana*," *Gene 10*: 131–136 (1991).

T. Furuya, et al., "Production of Tocopherols by Cell Culture of Safflower," *Phytochemistry 26*(10): 2741–2747 (1987).

I. Garcia, et al., "Subcellular localization and purification of a p–hydroxyphenylpyruvate dioxygenase from cultured carrot cells and characterization of the corresponding cDNA," *Biochem. J. 325*, 761–769 (1997).

S.K. Goers, et al., "Separation and characterization of two chorismate–mutase isoenzymes from *Nicotiana silvestris*," *Planta 162*: 109–116 (1984).

M. Harker, et al., "Biosynthesis of ketocarotenoids in transgenic cyanobacteria expressing the algal gene for β–C–4–oxygenase, crtO," *FEBS Letters 404*: 129–134 (1997).

K. M. Herrmann, "The Shikimate Pathway as an Entry to Aromatic Secondary Metabolism," *Plan Physiol. 107*: 7–12 (1995).

S. Kajiwara, et al., "Isolation and functional identification of a novel cDNA for astaxanthin biosynthesis from *Haematococcus pluvialis*, and astaxanthin synthesis in *Escherichia coli*," *Plant Molecular Biology 29*: 343–352, 1995.

Y. Keller, et al., "Metabolic compartmentation of plastid prenyllipid biosyntheses, Evidence for the involvement of a multifunctional geranylgeranyl reductase," *Eur. J. Biochem. 251*, 413–417 (1998).

G. M. Kishore, et al., "Amino Acid Biosynthesis Inhibitors as Herbicides," *Ann. Rev. Biochem. 57*:627–663 (1988).

M. H. Kumagai, et al., "Cytoplasmic inhibition of carotenoid biosynthesis with virus–derived RNA," *Proc. Natl. Acad. Sci. USA 92*: 1679–1683, (Feb. 1995).

T. Lotan, et al., "Cloning and expression in *Escherichia coli* of the gene encoding β–C–4–oxygenase, that converts β–carotene to the ketocarotenoid canthaxanthin in *Haematococcus pluvialis*," *FEBS Letters 364*: 125–128 (1995).

P. S. Marshall, et al., "Biosynthesis of Tocopherols: A Re–Examination of the Biosynthesis and Metabolism of 2–Methyl–6–Phytyl–1,4–Benzoquinol," *Phytochemistry 24*(8): 1705–1711 (1985).

N. Misawa, et al., "Elucidation of the *Erwinia uredovora* Carotenoid Biosynthetic Pathway by Functional Analysis of Gene Products Expressed in *Escherichia coli*," *Journal of Bacteriology* 6704–6712 Dec. 1990.

N. Misawa, et al., "Expression of an Erwinia phytoene desaturase gene not only confers multiple resistance to herbicides interfering with carotenoid biosynthesis but also alters xanthophyll metabolism in transgenic plants," *The Plant Journal 6*(4): 481–489 (1994).

N. Misawa, et al., "Functional expression of the *Erwinia uredovora* carotenoid biosynthesis gene crtI in transgenic plants showing an increase of β–carotene biosynthesis activity and resistance to the bleaching herbicide norflurazon," *The Plant Journal 4*(5): 833–840 (1993).

N. Misawa, et al., "Structure and Functional Analysis of a Marine Bacterial Carotenoid Biosynthesis Gene Cluster and Astaxanthin Biosynthetic Pathway Proposed at the Gene Level," *Journal of Bacteriology 177*(22): 6575–6584 (Nov. 1995).

C. Napoli, et al., "Introduction of a Chimeric Chalcone Synthase Gene into Petunia Results in Reversible Co–Suppression of Homologous Genes in trans," *The Plant Cell.2*: 279–289, (Apr. 1990).

S. R. Norris, et al., "Complementation of the Arabidopsis pds1 Mutation with the Gene Encoding p–Hydroxyphenylpyruvate Dioxygenase," *Plant Physiol. 117*: 1317–1323 (1998).

S. R. Norris, et al., "Genetic Dissection of Carotenoid Synthesis in Arabidopsis Defines Plastoquinone as an Essential Component of Phytoene Desaturation," *The Plant Cell 7*: 2139–2149 (Dec. 1995).

A. Oommen, et al., "The Elicitor–Inducible Alfalfa Isoflavone Reductase Promoter Confers Different Patterns of Developmental Expression in Homologous and Heterologous Transgenic Plants," *The Plant Cell 6*: 1789–1803, (Dec. 1994).

C. Peisker, et al., "Phytol and the Breakdown of Chlorophyll in Senescent Leaves," *J. Plant Physiol. 135*: 428–432 (1989).

D. L. Pompliano, et al., "Probing Lethal Metabolic Perturbations in Plants with Chemical Inhibition of Dehydroquinate Synthase," *J. Am. Chem. Soc.111*: 1866–1871 (1989).

Raven, et al., eds., Biology of Plants, Worth publs., $5^{th}$ edition, 629–30 (1992).

S. Römer, et al., "Expression of the Genes Encoding the Early Carotenoid Biosynthetic Enzymes in *Capsicum annuum*," *Biochemical and Biophysical Research Communications 196*(3): 1414–1421 (Nov. 15, 1993).

C. Ruzafa, et al., "The protein encoded by the *Shewanella colwelliana melA* gene is a p–hydroxyphenylpyruvate dioxygenase," *FEMS Microbiology Letters 124*: 179–184 (1994).

G. Sandmann, et al., "New functional assignment of the carotenogenic genes crtB and crtE with constructs of these genes from Erwinia species," *FEMS Microbiology Letters 90*: 253–258 (1992).

C. K. Shewmaker, et al., "Seed–specific overexpression of phytoene synthase: increase in carotenoids and other metabolic effects," *The PlanT Journal 20*(4): 401–412 (1999).

S. Shigeoka, et al., "Isolation and properties of γ–tocopherol methyltransferase in *Euglena gracilis*," *Biochimica et Biophysica Acta 1128*: 220–226 (1992).

B. K. Singh, et al., "Chorismate Mutase Isoenzymes from Sorghum bicolor: Purification and Properties," *Archives of Biochemistry and Biophysics 243*(2): 374–384 (Dec. 1985).

C.J.S. Smith, et al., "Antisense RNA inhibition of polygalacturonase gene expression in transgenic tomatoes," *Nature 334*: 724–726 (Aug. 25, 1998).

J. Soll, et al., "Tocopherol and Plastoquinone Synthesis in Spinach Chloroplasts Subfractions," *Archives of Biochemistry and Biophysics 204*(2): 544–550 (Oct. 15, 1980).

J. Soll, et al., "Hydrogenation of Geranylgeraniol," *Plant Physiol. 71*: 849–854 (1983).

A. Stocker, et al., "The Substrate Specificity of Tocopherol Cyclase," *Bioorganic & Medicinal Chemistry 4*(7): 1129–1134 (1996).

Z. Sun, et al., "Cloning and Functional Analysis of the β–Carotene Hydroxylase of *Arabidopsis thaliana*," *The Journal of Biological Chemistry 271*(40): 24349–24352 (Oct. 4, 1996).

J. A. Suzich, et al., "3–Deoxy–D–arabino–Heptulosonate 7–Phosphate Synthase from Carrot Root (*Daucus carota*) Is a Hysteretic Enzyme," *Plant Physiol. 79*: 765–770 (1985).

I. Verwoert, et al., "Developmental specific expression and organelle targeting of the *Escherichia coli fabD* gene, encoding malonyl coenzyme A–acyl carrier protein transacylase in transgenic rape and tobacco seeds," *Plant Molecular Biology 26*: 189–202 (1994).

E. Yamamoto, "Purification and Metal Requirements of 3–Dehydroquinate Synthase from *Phaseolus mungo* Seedlings," *Phytochemistry 19*: 779–781(1980).

S. Zaka, et al., "Changes in Carotenoids and Tocopherols During Maturation of Cassia Seeds," *Pakistan J. Sci. Ind. Res.30*(11): 812–14 (Nov. 1987).

X. Zhu, et al., "Cloning and Functional Expression of a Novel Geranylgeranyl Pyrophosphate Synthase Gene from *Arabidopsis thaliana* in *Escherichia coli*," *Plant Cell Physiol. 38*(3): 357–361 (1997).

\* cited by examiner

BglII
AGATCTGCTA GAGAGCTTTG CAATTCATAC AGAAGTGAGA AAAATGGCTT CTATGATATC    60

CTCTTCCGCT GTGACAACAG TCAGCCGTGC CTCTAGGGGG CAATCCGCCG CAGTGGCTCC   120

ATTCGGCGGC CTCAAATCCA TGACTGGATT CCCAGTGAAG AAGGTCAACA CTGACATTAC   180

TTCCATTACA AGCAATGGTG GAAGAGTAAA GTGCATGAAT AATCCGTCGT TACTCAATCA   240

TGCGGTCGAA ACGATGGCAG TTGGCTCGAA AAGTTTTGCG ACAGCCTCAA AGTTATTTGA   300

TGCAAAAACC CGGCGCAGCG TACTGATGCT CTACGCCCTGG TGCCGCCATT GTGACGATGT   360

TATTGACGAT CAGACGCTGG GCTTTCAGGC CCGGCAGCCT GCCTTACAAA CGCCCGAACA   420

ACGTCTGATG CAACTTGAGA TGAAAACGCG CCAGGCCTAT GCAGGATCGC AGATGCACGA   480

ACCGGCGTTT GCGGCTTTTC AGGAAGTGGC TATGGCTCAT GATATCGCCC CGGCTTACGC   540

GTTTGATCAT CTGGAAGGCT TCGCCATGGA TGTACGCGAA GCGCAATACA GCCAACTGGA   600

TGATACGCTG CGCTATTGCT ATCACGTTGC AGGCGTTGTC GGCTTGATGA TGGCGCAAAT   660

FIGURE 1

```
CATGGGCGTG CGGGATAACG CCACGCTGGA CCCGCGCCTGT GACCCTTGGGC TGGCATTTCA    720

GTTGACCAAT ATTGCTCGCG ATATTGTGGA CGATGCGCAT GCGGGCCGCT GTTATCTGCC    780

GGCAAGCTGG CTGGAGCATG AAGGTCTGAA CAAAGAGAAT TATGCGGCAC CTGAAAACCG    840

TCAGGCGCTG AGCCGTATCG CCCGTCGTTT GGTGCAGGAA GCAGAACCTT ACTATTTGTC    900

TGCCACAGCC GGCCTGGCAG GGTTGCCCCT GCGTTCCGCC TGGGCAATCG CTACGGCGAA    960

GCAGTTTTAC CGGAAAATAG GTGTCAAAGT TGAACAGGCC GGTCAGCAAG CCTGGGATCA   1020

GCGGCAGTCA ACGACCACGC CCGAAAAATT AACGCTGCTG CTGGCCCGCCT CTGGTCAGGC   1080

CCTTACTTCC CGGATGCGGG CTCATCCTCC CCGCCCTGCG CATCTCTGGC AGCGCCCGCT   1140

CTAGCGCCAT GTCTTTCCCG GAGCGTCCGA ATTATCGATG AATTCGAGCT CGGTACCCGG   1200

BamHI
GGATCCTCTA GAGTCGACCT GCAGGCATGC AA                                  1232
```

FIGURE 1 (continued)

| NAPIN PROMOTER | TP | CRT B | NAPIN 3' | NAPIN PROMOTER | AS E-CYCLASE | NAPIN 3' | 35SNPTII | pCGN 9002 - PHYTOENE SYNTHASE + ANTISENSE EPSILON CYCLASE

FIGURE 2E

| NAPIN PROMOTER | TP | CRT B | NAPIN 3' | NAPIN PROMOTER | AS B-CYCLASE | NAPIN 3' | 35SNPTII | pCGN 9017 - PHYTOENE SYNTHASE + ANTISENSE BETA CYCLASE

FIGURE 2F

```
           >AluI         >AluI                          >HaeIII |
             |             |                              |     |
             |   500       |        520                   |     |    540
           * |          *  |      *         *           | *   |        *
        CTTCTGGAGCAGCTTCTGGGAAGCTCTTGCAATACGAAGTTGGAGGGCCTAGAGTCTGTG

>HinfI      >Sau3AI
                                            |           |
                       560                  |  580      |          600
                  *          *         *    | *       | *            *
        TCCAAACTGCTTACGGCTTGGAGGTTGAGGTGGAAAAGAGTCCATATGATCCAGAGCAGA >AluI
                                                    |
                                   >MspI            |       >AluI
                                     |              |         |
                       620         640 |            |         |   660
                  *          *       * |            |  *     |      *
        TGGTGTTCATGGATTACAGAGATTATACAAACGAGAAAATCCGGAGCTTAGAAGCTGAAT >HinfI
                                            |
                       680                  700                    720
                  *          *         *     *         *             *
        ATCCAACGTTTCTCTACGCCATGCCTATGACAAAGACCAGAGTCTTCTTTGAGGAGACAT >AluI
                                                  |
                       740                760     |                780
                  *          *         *     *   | *                *
        GTCTTGCTTCAAAAGATGTCATGCCCTTTGATTTGCTTAAAAAGAAGCTCTTGTTGAGAT >HinfI
           |
           |   800                  820                            840
         * |     *         *         *         *         *           *
        TAGAGACACTCGGAATCCGAATACTAAAGACTTACGAAGAGGAATGGTCTTATATCCCAG >AluI
                                                             |
                              >HinfI                       >PstI
                                |                           ||
                       860      |         880             * ||           900
                  *          *  | *         *             * ||            *
        TAGGTGGTTCCTTGCCAAACACGGAACAAAAGAATCTCGCCTTTGGCGCTGCAGCTAGCA >SpeI    >BamHI
                                                           |        |
                       >EcoRI   >BstXI    >HaeIII |      >Sau3AI
                         |        |         |    |        |
                   920   |        |  940    |    |        |         960
                  *      *      *   | *     | *  |      | *        | *
        TGGTACATCCCGCAACAGAAGCCGAATTCCAGCACACTGGCGGCCGTTACTAGTGGATCC
        GA
```

```
GAGCTCGGAT CCACTAGTAA CGGCCGCCAG TGTGCTGGAA TTCGGCTTCT ATCTTGTACC    60
                                                                    *
AAATTGTTGA TCATCTTAGC AAGAGGAACA GTTCCCTTCG TCATGATCTC CAACCTCGAG   120
                                                                    *
GTATTAGAAG CATGCGAGAA GAGCGACAGC CCGAAGAACA CCAGGTCCGG GAGAAACAGC   180
                                                                    *
CTCGACGACA AGAAACCATG CCAGTAACGC GGTTCCAGGT CAAAGAACGC ATCAAAGAAC   240
                                                                    *
CTCCTAGTAG CATCCAAATC AAGCTTCAGC AAAATATCCA TCCCAAAACA GAAGAACTCC   300
                                                                    *
CTCTGTCTCC GCCTCTCAAT AGGCCACAAG TCTCTCCACA CCTCAGCCGA GAGCTCATCT   360
                                                                    *
CCTCTCAAGC CGTTGTTGTT ACCACCACCA AGGTACCGCA CTATAGCGTT TGCAACTATC   420
                                                                    *
GGAGCAGCTG CAAGAGTCCT AGCAACCATG TAACCAGTCG AAGGATGAAC CATCCCCGCC   480
                                                                    *
GTACCGCCAA TGCCAACAAC TCTTTGAGGC AAGACCGGTA AAGGACCTCC CATAGGGATC   540
                                                                    *
```

FIGURE 11

```
ACACAACGCT CGTCTTCCTC AATCCGCTTC ACGTTGATCC CCAAATGTTT CAGCCTCGCA
                                                                  600
                                                                   *

ACCATCCTCT CTTGGATATC TTCCATCTTC AGACCCGGCC TAGCCACAAG AGACGTCTCT
                                                                  660
                                                                   *

TCAAGAAAGA TCCTGTTGGA AGAAAACGGC ATCGCGTACA GGAACGTAGG GATCTTGCTG
                                                                  720
                                                                   *

TTCCGCTCTT TAACCTCAGG GTACGCGGTCA AGATGCTTAT CTCTCCAGTC CATGAACACC
                                                                  780
                                                                   *

ATCTTATCCA CATCAAACGG GTGACCATCG ACCTCAGCAA TGATACCATA AGCTACTTGA
                                                                  840
                                                                   *

TACCCAGGGT TATAAGGCTT ATCATACTGA ACCAAGCATC TTGAAAAACC AGTAGGGTCG
                                                                  900
                                                                   *

AGAACAACAG AAGCCTGAAT CTTCACACCG TCACTGCAGA CAACAGTGGA GTTAACCTCC
                                                                  960
                                                                   *

TCGTGAACCA CGTCAGTGAC TTTAGCCTGA TGGAATCTAA CACCGTTGGT GATGCACTTC
                                                                 1020
                                                                   *

TGAAGCATCT TGGATTTGAG CTGTTTACGG TTCACTCTCC CGTAAGGCCG GGACAGGTCC
                                                                 1080
                                                                   *
```

FIGURE 11 (continued)

```
                                                                  1140
                                                                     •
TTTTCGGAGC CGTCGTTGAT GTAGACGACG GCGCCGGACC AGGTGGTGTC GAGGCAGTCT

1200
                                                                     •
AGCAAGTCCA TGGCTTCGAA CTCGTCAACC CAAACTCCGT AGTTGTTAGG CCAAATGAGT

1260
                                                                     •
TTGCGGGAAG GATCGATGGA GCAGACAGAG AGTCCAGCTT CGGAGACTTG CTGAGCCACG

1320
                                                                     •
GCTAAACCAG CGGGGCCGCC GCCAACGATA GCTAGATCAA CAACTTTGTT CAGGGAAGTG

1380
                                                                     •
TCGTTTAAAG GAAGGTCCAA GTCGAGATTC TCCTTCTTGG TTTCAGGAAC AAGATCCAAA

1440
                                                                     •
AGAGCACTAC TAGCACTAGT GATACTACTA CCGATTCTGA TTGCTCTTTT CTTCAAACCA

1500
                                                                     •
AGCTTAACCC TTGAAGGATT TGGACTTAAT CTCTCGAACC CATGAAACTG AGGGATGAAA

1560
                                                                     •
AACTCGAGCT TGTTGGGTGT TTTCAACAGA GTATCCATCG AATTCTGCAG ATATCCATCA

CACTGGCGGC CGCTCGAGCA TGCATCTAGA
```

FIGURE 11 (continued)

| Sample ID # | Segregation ratio | Lutein | Lycopene | α-Carotene | β-Carotene | Total |
|---|---|---|---|---|---|---|
| SP30021 control 1 | | 24.4 | ND | ND | 1.9 | 26.3 |
| SP30021 control 2 | | 34.0 | ND | ND | 4.9 | 38.9 |
| T2 3390-SP30021-1 | 3:1 | 33.5 | 6.1 | 229.0 | 385.7 | 654.3 |
| T2 3390-SP30021-2 | 15:1 | 50.4 | 6.2 | 372.4 | 721.4 | 1150.4 |
| T2 3390-SP30021-3 | no fit | 45.8 | 3.9 | 352.9 | 580.9 | 983.5 |
| T2 3390-SP30021-4 | 3:1 | 31.0 | 4.9 | 306.1 | 463.3 | 805.3 |
| T2 3390-SP30021-5 | 3:1 | 36.8 | 10.5 | 370.6 | 659.4 | 1077.3* |
| T2 3390-SP30021-6 | 15:1 | 46.9 | 9.1 | 445.1 | 797.0 | 1298.1 |
| T2 3390-SP30021-7 | 15:1 | 51.2 | 7.4 | 494.9 | 941.4 | 1494.9 |
| T2 3390-SP30021-8 | no fit | 41.9 | 11.3 | 468.4 | 904.3 | 1425.9 |
| T2 3390-SP30021-9 | >63:1 | 68.4 | 11.9 | 394.2 | 949.2 | 1423.7 |
| T2 3390-SP30021-10 | null | 51.6 | ND | 12.6 | 22.8 | 87.0 |
| T2 3390-SP30021-11 | 3:1 | 52.2 | 9.5 | 409.8 | 714.5 | 1186.0* |
| T2 3390-SP30021-12* | 3:1 | 48.0 | 10.2 | 400.0 | 738.8 | 1197.0* |
| T2 3390-SP30021-13 | 3:1 | 66.1 | 3.9 | 98.1 | 216.0 | 384.1 |
| T2 3390-SP30021-14 | 3:1 | 49.1 | 8.9 | 320.0 | 611.6 | 989.6 |
| T2 3390-SP30021-15 | null | 27.0 | ND | ND | 1.2 | 28.2 |
| T2 3390-SP30021-16 | 3:1 | 55.6 | 6.4 | 283.1 | 527.4 | 872.5 |
| T2 3390-SP30021-17 | 3:1 | 53.0 | 9.1 | 324.9 | 614.3 | 1001.3 |
| T2 3390-SP30021-18 | >63:1 | 49.6 | 8.1 | 449.0 | 759.3 | 1266.0 |
| T2 3390-SP30021-19 | 3:1 | 62.2 | 7.6 | 346.1 | 613.2 | 1029.1 |
| T2 3390-SP30021-20 | 3:1 | 52.1 | 6.3 | 285.0 | 544.9 | 888.3 |
| T2 3390-SP30021-21 | 3:1 | 56.2 | 4.1 | 187.9 | 334.2 | 582.4 |
| T2 3390-SP30021-22 | null | 43.1 | ND | ND | 4.9 | 48.0 |
| T2 3390-SP30021-23 | 3:1 | 71.0 | 10.9 | 358.6 | 693.9 | 1134.4* |
| T2 3390-SP30021-24 | no fit | 53.9 | 7.3 | 272.1 | 520.4 | 853.7 |
| T2 3390-SP30021-25 | 3:1 | 31.9 | 12.2 | 309.1 | 580.9 | 934.1 |
| T2 3390-SP30021-26* | 3:1 | 34.3 | 9.3 | 311.2 | 584.4 | 939.2* |
| T2 3390-SP30021-27 | 3:1 | 52.6 | 9.8 | 299.8 | 686.3 | 1048.5* |
| T2 3390-SP30021-28 | no fit | 68.4 | 10.0 | 446.3 | 907.7 | 1432.4 |
| T2 3390-SP30021-29 | >63:1 | 85.1 | 8.5 | 459.4 | 822.9 | 1375.9 |
| T2 3390-SP30021-30 | 3:1 | 63.7 | 5.8 | 356.9 | 598.4 | 1024.8 |
| T2 3390-SP30021-31 | 3:1 | 76.0 | 7.3 | 302.5 | 527.1 | 912.9 |
| T2 3390-SP30021-32 | null | 51.8 | 2.3 | 31.4 | 55.0 | 140.5 |
| T2 3390-SP30021-33 | 3:1 | 36.3 | 8.9 | 283.1 | 546.9 | 875.2 |
| T2 3390-SP30021-34 | >63:1 | 86.9 | 12.1 | 502.3 | 808.3 | 1409.6 |
| T2 3390-SP30021-35 | 3:1 | 39.3 | 8.1 | 224.5 | 461.0 | 732.9 |
| T2 3390-SP30021-36 | 15:1 | 55.5 | 11.0 | 538.5 | 829.9 | 1434.9 |
| T2 3390-SP30021-37* | 3:1 | 50.3 | 10.0 | 291.1 | 625.9 | 977.3* |
| T2 3390-SP30021-38 | 3:1 | 70.5 | 8.1 | 309.0 | 576.1 | 963.7 |
| T2 3390-SP30021-39 | null | 37.3 | ND | ND | 3.6 | 40.9 |
| T2 3390-SP30021-40 | 3:1 | 37.5 | 1.8 | 251.1 | 505.2 | 796.0 |
| T2 3390-SP30021-41 | 3:1 | 47.5 | 8.4 | 414.1 | 719.3 | 1189.3* |
| T2 3390-SP30021-42 | 3:1 | 42.6 | 5.1 | 230.3 | 352.9 | 630.9 |
| T2 3390-SP30021-43 | no fit | 83.3 | 5.6 | 128.4 | 219.8 | 437.9 |
| T2 3390-SP30021-46 | 3:1 | 21.6 | 1.4 | 211.2 | 368.3 | 602.5 |
| T2 3390-SP30021-47 | 3:1 | 79.1 | 3.7 | 312.5 | 570.5 | 965.8 |
| T2 3390-SP30021-48 | 3:1 | 45.3 | 3.0 | 225.2 | 401.5 | 675.0 |
| T2 3390-SP30021-49 | 15:1 | 28.3 | 1.6 | 346.0 | 677.2 | 1053.1 |
| T4 3390-SP001-1-6-13 | Homo | 52.4 | 1.5 | 439.5 | 669.3 | 1162.7 |

FIGURE 12

| Sample ID # | Segregation status | Carotenoid concentration (μg/gFW) | | | | |
|---|---|---|---|---|---|---|
| | | Lutein | Lycopene | α-Carotene | β-Carotene | Total |
| T3 3390-SP001-4-12 | Homo | 43.9 | 17.2 | 282.1 | 636.8 | 980.0 |
| T3 3390-SP001-5-7 | Het | 50.7 | 6.3 | 190.6 | 386.8 | 634.4 |
| T3 3390-SP001-5-12 | Homo | 45.5 | 19.5 | 255.9 | 633.4 | 954.3 |
| T3 3390-SP001-11-6 | Homo | 46.5 | 12.8 | 372.2 | 538.4 | 969.9 |
| T3 3390-SP001-11-9 | Homo | 54.0 | 10.2 | 406.0 | 556.0 | 1026.2 |
| T3 3390-SP001-14-2 | Homo | 59.7 | 12.5 | 342.4 | 764.0 | 1178.6 |
| T3 3390-SP001-14-6 | Homo | 66.3 | 12.9 | 431.0 | 673.9 | 1184.1 |
| T3 3390-SP001-15-9 | Homo | 30.8 | 14.3 | 271.8 | 559.8 | 876.7 |
| T3 3390-SP001-15-12 | Homo | 39.6 | 13.1 | 241.7 | 649.1 | 943.5 |
| T3 3390-SP001-16-3 | Homo | 49.9 | 17.1 | 230.2 | 519.7 | 816.9 |
| T3 3390-SP001-16-6 | Homo | 35.5 | 21.1 | 263.8 | 547.7 | 868.1 |
| T3 3390-SP001-35-2 | Het | 37.6 | 7.2 | 125.4 | 313.9 | 484.1 |
| T3 3390-SP001-35-10 | Homo | 43.7 | 16.6 | 234.7 | 503.9 | 798.9 |
| T3 3390-SP001-35-12 | Homo | 50.2 | 21.3 | 361.7 | 695.7 | 1128.9 |
| T3 3390-SP001-8-3 | Het | 41.4 | 9.9 | 178.2 | 434.4 | 663.9 |
| T3 3390-SP001-8-9 | Homo | 39.1 | 18.2 | 309.3 | 505.0 | 871.6 |
| T3 3390-SP001-8-11 | Homo | 35.9 | 19.6 | 260.7 | 580.4 | 896.6 |
| T3 3390-SP001-18-8 | Het | 29.2 | 12.2 | 112.1 | 247.6 | 441.1 |
| T3 3390-SP001-16-10 | Het | 38.0 | 14.6 | 248.2 | 486.3 | 787.1 |
| T4 3390-SP001-1-6-1 | Homo | 27.8 | 20.5 | 248.7 | 379.1 | 676.1 |
| T4 3390-SP001-1-6-8 | Homo | 38.5 | 16.8 | 304.1 | 383.9 | 743.3 |
| VAR SP001-4-5 | | 54.2 | ND | ND | 5.8 | 60.0 |
| VAR SP001-4-6 | | 51.2 | ND | ND | 7.0 | 58.2 |
| VAR SP001-4-10 | | 30.2 | ND | ND | ND | 30.2 |

FIGURE 13

SEQUENCE LISTING

```
<160> NUMBER OF SEQ ID NOS: 4

<210> SEQ ID NO 1
<211> LENGTH: 1232
<212> TYPE: DNA
<213> ORGANISM: Erwinia uredovora

<400> SEQUENCE: 1
agatctgcta gagagctttg caattcatac agaagtgaga aaaatggctt ctatgatatc      60
ctcttccgct gtgacaacag tcagccgtgc ctctagggg caatccgccg cagtggctcc     120
```

-continued

```
attcggcggc ctcaaatcca tgactggatt cccagtgaag aaggtcaaca ctgacattac    180
ttccattaca agcaatggtg aagagtaaa gtgcatgaat aatccgtcgt tactcaatca    240
tgcggtcgaa acgatggcag ttggctcgaa aagttttgcg acagcctcaa agttatttga    300
tgcaaaaacc cggcgcagcg tactgatgct ctacgcctgg tgccgccatt gtgacgatgt    360
tattgacgat cagacgctgg gctttcaggc cggcagcct gccttacaaa cgcccgaaca    420
acgtctgatg caacttgaga tgaaaacgcg ccaggcctat gcaggatcgc agatgcacga    480
accggcgttt gcggcttttc aggaagtggc tatggctcat gatatcgccc ggcttacgc    540
gtttgatcat ctggaaggct cgccatgga tgtacgcgaa gcgcaataca gccaactgga    600
tgatacgctg cgctattgct atcacgttgc aggcgttgtc ggcttgatga tggcgcaaat    660
catgggcgtg cgggataacg ccacgctgga ccgcgcctgt gaccttgggc tggcatttca    720
gttgaccaat attgctcgcg atattgtgga cgatgcgcat gcgggccgct gttatctgcc    780
ggcaagctgg ctggagcatg aaggtctgaa caaagagaat tatgcggcac ctgaaaaccg    840
tcaggcgctg agccgtatcg cccgtcgttt ggtgcaggaa gcagaacctt actatttgtc    900
tgccacagcc ggcctggcag ggttgcccct gcgttccgcc tgggcaatcg ctacggcgaa    960
gcaggtttac cggaaaatag gtgtcaaagt tgaacaggcc ggtcagcaag cctgggatca   1020
gcggcagtca acgaccacgc cgaaaaaatt aacgctgctg ctggccgcct ctggtcaggc   1080
ccttacttcc cggatgcggg ctcatcctcc ccgccctgcg catctctggc agcgcccgct   1140
ctagcgccat gtctttcccg gagcgtccga attatcgatg aattcgagct cggtacccgg   1200
ggatcctcta gagtcgacct gcaggcatgc aa                                1232
```

<210> SEQ ID NO 2
<211> LENGTH: 960
<212> TYPE: DNA
<213> ORGANISM: Brassica napus

<400> SEQUENCE: 2

```
tgaattgtaa tacgactcac tatagggcga attggcccct ctagatgcat gctcgagcgg     60
ccgccagtgt gatggatatc tgcagaattc ggcttgtttg tggtcctgct ggtttagcct    120
tggctgcaga atcagcaagg ttaggtctca agttggact cattggtcct gatcttcctt    180
tcactaacaa ctacggtgtt tgggaagatg agttcaacga tcttggcttg caaaaatgta    240
ttgagcatgt ttggagagat acccttgtgt atctggacga tgacaatcct attaccattg    300
gtcgtgctta tggaagagtt agtcgacgtt tacttcacga ggagctcttg aggaggtgtg    360
tggagtcagg tgtctcgtat cttagctcca aagttgagag cataacagaa gctcctgatg    420
gccttaggct tgtttcctgt gaacaaaaca cccttgttcc gtgcaggctt gccactgttg    480
cttctggagc agcttctggg aagctcttgc aatacgaagt tggagggcct agagtctgtg    540
tccaaactgc ttacggcttg gaggttgagg tggaaaagag tccatatgat ccagagcaga    600
tggtgttcat ggattacaga gattatacaa acgagaaaat ccggagctta gaagctgaat    660
atccaacgtt tctctacgcc atgcctatga caaagaccag agtcttcttt gaggagacat    720
gtcttgcttc aaaagatgtc atgcccttttg atttgcttaa aaagaagctc ttgttgagat    780
tagagacact cggaatccga atactaaaga cttacgaaga ggaatggtct tatatcccag    840
taggtggttc cttgccaaac acggaacaaa agaatctcgc cttttggcgct gcagctagca    900
tggtacatcc cgcaacagaa gccgaattcc agcacactgg cggccgttac tagtggatcc    960
```

<210> SEQ ID NO 3
<211> LENGTH: 1272
<212> TYPE: DNA
<213> ORGANISM: Brassica napus

<400> SEQUENCE: 3

| | | | | | |
|---|---|---|---|---|---|
| gtgaattgta | atacgactca | ctatagggcg | aattggccct | tctagatgca | tgctcgagcg | 60 |
| gccgccagtg | tgatggatat | ctgcagaatt | cggcttgttt | gtggtcctgc | tggtttagcc | 120 |
| ttggcggctg | aatcagctaa | gttaggactt | aaagttggac | tgattggtcc | tgaccttcct | 180 |
| ttcactaaca | actacggtgt | tgggaagat | gagttcaacg | atcttggctt | gcaaaaatgt | 240 |
| attgagcatg | tttggagaga | tacccttgtg | tatctggacg | atgacaatcc | tattaccatt | 300 |
| ggtcgtgctt | atggaagagt | tagtcgacgt | ttacttcacg | aggagttctt | gaggaggtgt | 360 |
| gtggagtcag | gtgtctcgta | tcttagctcc | aaagttgaga | gcataacaga | agctcctgat | 420 |
| ggccttaggc | ttgttttcctg | tgaacaaaac | acccttgttc | cgtgcaggct | tgccactgtt | 480 |
| gcttctggag | cagcttctgg | gaagctcttg | caatacgaag | ttggagggcc | tagagtctgt | 540 |
| gtccaaactg | cttacggctt | ggaggttgag | gtggaaaaga | gtccatatga | tccagagcag | 600 |
| atggtgttca | tggattacag | agattataca | aacgagaaaa | tccggagctt | agaagctgaa | 660 |
| tatccaacgt | ttctctacgc | catgcctatg | acaaagacca | gagtcttctt | tgaggagaca | 720 |
| tgtcttgctt | caaaagatgt | catgccccttt | gatttgctta | aaagaagct | cttgttgaga | 780 |
| ttagagacac | tcggaatccg | aatactaaag | acttacgaag | aggaatggtc | ttatatccca | 840 |
| gtaggtggtt | ccttgccaaa | cacggaacaa | agaatctcg | cctttggtgc | tgcagctagc | 900 |
| atggttcatc | ctgcaacagg | ctattcagtt | gtgagatcct | tgtctgaagc | tccaaaatac | 960 |
| gcatcagtca | tcgctaatat | actaaaacat | gagaccacta | cttccttcac | cagacacatc | 1020 |
| aacaccaata | tttcaagaca | agcttgggat | actttatggc | caccagaaag | gaaacgacag | 1080 |
| agagcattct | ttctaagccg | aattccagca | cactggcggc | cgttactagt | ggatccgagc | 1140 |
| tcggtaccaa | gcttggcgta | atcatggtca | tagctgtttc | ctgtgtgaaa | ttgttatccg | 1200 |
| ctcacaattc | cacacaacat | acgagccgga | agcataaagt | gtaaagcctg | gggtgcctaa | 1260 |
| tgagtgagct | aa | | | | | 1272 |

<210> SEQ ID NO 4
<211> LENGTH: 1590
<212> TYPE: DNA
<213> ORGANISM: Brassica napus

<400> SEQUENCE: 4

| | | | | | |
|---|---|---|---|---|---|
| gagctcggat | ccactagtaa | cggccgccag | tgtgctggaa | ttcggcttct | atcttgtacc | 60 |
| aaattgttga | tcatcttagc | aagaggaaca | gttcccttcg | tcatgatctc | caacctcgag | 120 |
| gtattagaag | catgcgagaa | gagcgacagc | ccgaagaaca | ccaggtccgg | gagaaacagc | 180 |
| ctcgacgaca | agaaaccatg | ccagtaacgc | ggttccaggt | caagaacgc | atcaaagaac | 240 |
| ctcctagtag | catccaaatc | aagcttcagc | aaaatatcca | tcccaaaaca | gaagaactcc | 300 |
| ctctgtctcc | gcctctcaat | aggccacaag | tctctccaca | cctcagccga | gagctcatct | 360 |
| cctctcaagc | cgttgttgtt | accaccacca | aggtaccgca | ctatagcgtt | tgcaactatc | 420 |
| ggagcagctg | caagagtcct | agcaaccatg | taaccagtcg | aaggatgaac | catccccgcc | 480 |
| gtaccgccaa | tgccaacaac | tctttgaggc | aagaccggta | aaggacctcc | catagggatc | 540 |
| acacaacgct | cgtcttcctc | aatccgcttc | acgttgatcc | ccaaatgttt | cagcctcgca | 600 |

```
accatcctct cttggatatc ttccatcttc agacccggcc tagccacaag agacgtctct      660
tcaagaaaga tcctgttgga agaaaacggc atcgcgtaca ggaacgtagg gatcttgctg      720
ttccgctctt taacctcagg gtacgcgtca agatgcttat ctctccagtc catgaacacc      780
atcttatcca catcaaacgg gtgaccatcg acctcagcaa tgataccata agctacttga      840
tacccagggt tataaggctt atcatactga accaagcatc ttgaaaaacc agtagcgtcg      900
agaacaacag aagcctgaat cttcacaccg tcactgcaga caacagtgga gttaacctcc      960
tcgtgaacca cgtcagtgac tttagcctga tggaatctaa caccgttggt gatgcacttc     1020
tgaagcatct tggatttgag ctgtttacgg ttcactctcc cgtaaggccg ggacaggtcc     1080
ttttcggagc cgtcgttgat gtagacgacg gcgccggacc aggtggtgtc gaggcagtct     1140
agcaagtcca tggcttcgaa ctcgtcaacc caaactccgt agttgttagg ccaaatgagt     1200
ttgggggaag gatcgatgga gcagacagag agtccagctt cggagacttg ctgagccacg     1260
gctaaaccag cggggccgcc gccaacgata gctagatcaa caactttgtt cagggaagtg     1320
tcgtttaaag gaaggtccaa gtcgagattc tccttcttgg tttcaggaac aagatccaaa     1380
agagcactac tagcactagt gatactacta ccgattctga ttgctctttt cttcaaacca     1440
agcttaaccc ttgaaggatt tggacttaat ctctcgaacc catgaaactg agggatgaaa     1500
aactcgagct tgttgggtgt tttcaacaga gtatccatcg aattctgcag atatccatca     1560
cactggcggc cgctcgagca tgcatctaga                                      1590
```

METHODS FOR PRODUCING CAROTENOID COMPOUNDS AND SPECIALTY OILS IN PLANT SEEDS

CROSS-REFERENCE TO RELATED APPLICATIONS

This application is a continuation of U.S. application Ser. No. 08/908,758, filed Aug. 8, 1997, now U.S. Pat. No. 6,429,356, which claims priority to U.S. Provisional Application Ser. No. 60/024,145, filed Aug. 9, 1996, now expired, each of which is herein incorporated in its entirety by reference.

precursor of vitamin A in mammals. Current methods for commercial production of β-carotene include isolation from carrots, chemical synthesis, and microbial production.

A number of crop plants and a single oilseed crop are known to have substantial levels of carotenoids, and consumption of such natural sources of carotenoids have been indicated as providing various beneficial health effects. The below table provides levels of carotenoids that have been reported for various plant species.

| Crop | Beta-Carotene | Alpha-Carotene | Lycopene | Lutein | Total |
|---|---|---|---|---|---|
| Carrots | 30–110 | 10–40 | 0–0.5 | 0–2 | 65–120 |
| Pepper (gr) | 2 | — | — | 2 | 8 |
| Pepper (red) | 15 | 1 | — | — | 200 |
| Pumpkin | 16 | 0.3 | tr | 26 | 100 |
| Tomato | 3–6 | — | 85 | — | 98 |
| Watemelon | 1 | tr | 19 | — | 25 |
| Marigold petals | 5 | 4 | — | 1350 | 1500 |
| Red palm oil | 256 | 201 | 8 | — | 545 |

CAROTENOID CONTENTS OF VARIOUS CROPS (μg/g)

INCORPORATION OF SEQUENCE LISTING

The Sequence Listing, provided in paper form, and a computer readable form of the sequence listing on diskette, containing the file named 16516141.txt, which is 7,150 bytes in size (measured in MS-DOS), and which was created on Jan. 9, 2002, are herein incorporated by reference.

1. Field of the Invention

The invention relates to genetic modification of plants, plant cells and seeds, particularly altering carotenoid biosynthesis and fatty acid composition.

2. Background of the Invention

Carotenoids are pigments with a variety of applications. They are yellow-orange-red lipids which are present in green plants, some molds, yeast and bacteria. Carotenoid hydrocarbons are referred to as carotenes, whereas oxygenated derivatives are referred to as xanthophylls. The carotenoids are part of the larger isoprenoid biosynthesis pathway which, in addition to carotenoids, produces such compounds as chlorophyll and tocopherols, Vitamin E active agents. The carotenoid pathway in plants produces carotenes, such as α- and β-carotene, and lycopene, and xanthophylls, such as lutein.

The biosynthesis of carotenoids involves the condensation of two molecules of the $C_{20}$ precursor geranyl $PP_i$ to yield the first $C_{40}$ hydrocarbon phytoene. In a series of sequential desaturations, phytoene yields lycopene. Lycopene is the precursor of the cyclic carotenes, β-carotene and α-carotene. The xanthophylls, zeaxanthin and lutein are formed by hydroxylation of β-carotene and α-carotene, respectively.

β-carotene, a carotene whose color is in the spectrum ranging from yellow to orange, is present in a large amount in the roots of carrots and in green leaves of plants. β-carotene is useful as a coloring material and also as a The pathway for biosynthesis of the carotenoids has been studied in a variety of organisms and the biosynthetic pathway has been elucidated in organisms ranging from bacteria to higher plants. See, for example, Britton, G. (1988) *Biosynthesis of carotenoids*, p. 133–182, In T. W. Goodwin (ed.), *Plant pigments*, 1988. Academic Press, Inc. (London), Ltd., London. Carotenoid biosynthesis genes have also been cloned from a variety of organisms including *Erwinia uredovora* (Misawa et al. (1990) *J. Bacteriol.* 172:6704–6712; *Erwinia herbicola* (Application WO 91/13078, Armstrong et al. (1990) *Proc. Natl. Acad. Sci., USA* 87:9975–9979); *R. capsulatus* (Armstrong et al. (1989) *Mol. Gen. Genet* 216:254–268, Romer et al. (1993) *Biochem. Biophys. Res. Commun.* 196:1414–1421); *Thermus thermophilus* (Hoshino et al. (1993) *Appl. Environ. Microbiol.* 59:3150–3153); the cyanobacterium Synechococcus sp. (Genbank accession number X63873). See also, application WO 96/13149 and the references cited therein.

While the genes have been elucidated, little is known about the use of the genes in plants. Investigations have shown that over expression or inhibition of expression of the plant phytoene synthase (Psy1) gene in transgenic plants can alter carotenoid levels in fruits. See, Bird et al. (1991) *Biotechnology* 9:635–639; Bramley et al. (1992) *Plant J.* 2:343–349; and Fray and Grierson (1993) *Plant Mol. Biol.* 22:589–602. Further, as reported by Fray et al. (1995) *The Plant Journal* 8:693–701, constitutive expression of a fruit phytoene synthase gene in transgenic tomatoes causes dwarfism by redirecting metabolites from the gibberellin pathway.

Application WO 96/13149 reports on enhancing carotenoid accumulation in storage organs such as tubers and roots of genetically engineered plants. The application is directed towards enhancing colored native carotenoid production in specific, predetermined non-photosynthetic storage organs. The examples of the application are drawn to increasing colored carotenoids in transformed carrot roots and in orange flesh potato tubers. Both of these tissues are vegetative tissues, not seeds, and natively have a high level of carotenoids.

Carotenoids are useful in a variety of applications. Generally, carotenoids are useful as supplements, particularly vitamin supplements, as vegetable oil based food products and food ingredients, as feed additives in aminal feeds and as colorants. Specifically, phytoene finds use in treating skin disorders. See, for example, U.S. Pat. No. 4,642,318. Lycopene, α- and β-carotene are used as food coloring agents. Consumption of β-carotene and lycopene has also been implicated as having preventative effects against certain kinds of cancers. In addition, lutein consumption has been associated with prevention of macular degeneration of the eye.

Plant oils are useful in a variety of industrial and edible applications. Novel vegetable oils compositions and/or improved means to obtain oils compositions, from biosynthetic or natural plant sources are needed. Depending upon the intended oil use, various different fatty acid compositions are desired. The demand for modified oils with specific fatty acid compositions is great, particularly for oils high in oleic acid. See, Haumann, B. F. (1996) *INFORM* 7:320–334. As reported by Haumann, the ideal frying oil would be a low-saturate, high oleic and low linolenic oil. Furthermore, studies in recent years have established the value of monounsaturated fatty acids as a dietary constituent.

Attempts have been made over the years to improve the fatty acid profiles of particular oils. For example, the oxidative stability of vegetable oil is related to the number of double bonds in its fatty acids. That is, molecules with several double bonds are recognized to be more unstable. Thus, scientists have attempted to reduce the content of α-linolenic acid in order to improve shelf life and oxidative stability, particularly under heat.

It is apparent that there is needed a method for producing significant levels of carotenoid compounds in crop plants and particularly in plant seeds. It would additionally be beneficial to alter the fatty acid content of the plants and seeds. Such altered seed products would be useful nutritionally as well as provide a source for producing more stable oils. There is no report of methods to substantially altering the levels and composition of carotenoids produced in a plant seed, particularly with respect to increasing the level of production of carotenoids. There is therefore needed, a useful method for altering carotenoid levels in plants, particularly seeds, and for producing oils with modified carotenoid composition and/or content.

SUMMARY OF THE INVENTION

Transformed plants, plant cells and seeds having altered carotenoid levels and/or modified fatty acid compositions are provided. The plants, plant cells and seeds are transformed with at least one carotenoid biosynthesis gene. Methods for making and using the transformed compositions of the invention are also provided. Methods find use in altering carotenoid levels in plants, particularly seeds, as well as increasing particular compounds for molecular farming, such as for production of particular carotenoids and tocopherols. At the same time, the transformed compositions, particularly seeds, provide a source of modified oils, which oils may be extracted from the seeds in order to provide an oil product comprising a natural source of various carotenoids and carotenoid mixtures. In a particular aspect of the present invention transformed seed can provide a source for particular carotenoid compounds and/or for modified speciality oils having altered carotenoid or tocopherol compostions and/or altered fatty acid composition, particularly having increased levels of oleic acid and decreased levels of linoleic and linolenic acids.

BRIEF DESCRIPTION OF THE FIGURES

FIG. 1 shows the nucleotide sequence (SEQ ID NO: 1) of the SSU/crtB fusion sequence.

FIG. 2 presents constructs for expression of carotenoid biosynthesis genes in plant seeds. FIG. 2E shows plasmid pCGN9002 which contains the napin promoter operably linked to the SSU/crtB sequence and the napin promoter operably linked to an antisense epsilon cyclase sequence. FIG. 2F shows plasmid pCGN9017 which contains the napin promoter operably linked to the SSU/crtB sequence and the napin promoter operably linked to an antisense beta cyclase sequence.

FIG. 11 provides sequence (SEQ ID NO: 4) of a *B. napus* beta cyclase cDNA clone.

FIG. 12 provides T2 seed analysis of 3390 transformed *Brassica napus* plants.

FIG. 13 provides T3 seed analysis of 3390 transformed *Brassica napus* plants.

DETAILED DESCRIPTION OF THE INVENTION

Figure 2A:
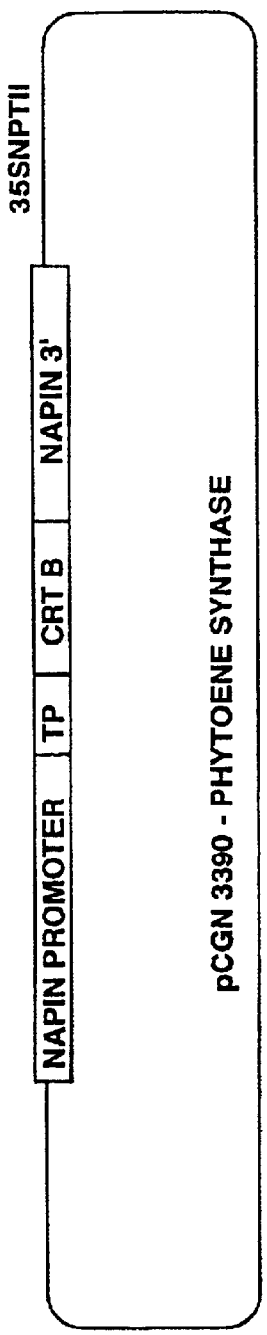
FIG. 2A shows plasmid pCGN3390 which contains the napin promoter operably linked to the SSU/crtB sequence.

In accordance with the subject invention, methods for increasing production of carotenoid compounds as well as for altering fatty acid compositions in a plant, particularly in plant seeds are provided. The method involves transforming a plant cell with at least one carotenoid biosynthesis gene. This has the effect of altering carotenoid biosynthesis particularly increasing the production of downstream products, as well as providing novel seed oils having desirable fatty acid compositions. A second gene can then be utilized to shunt the metabolic activity to the production of particular carotenoid compounds or to further alter the fatty acid composition.

Surprisingly it has been found that transformation of a plant with an early carotenoid biosynthesis gene leads to a significant increase in the flux through the carotenoid pathway resulting in an increase in particular carotenoids. That is, there is an increase in the metabolic activity that can be further manipulated for the production of specific carotenoids. In addition, the transformed seeds may demonstrate altered fatty acid compositions as the result of the carotenoid gene expression, such as seen with the seeds described herein from plants transformed with a phytoene synthase gene.

Thus, using the methods of the invention seeds are provided which produce high levels of a particular carotenoid and/or produce speciality oils having a desired fatty acid composition. In oilseed Brassica, for example, transformation with an early carotenoid biosynthesis gene leads to seeds having a significant increase in the production of α-carotene, β-carotene and lutein. In addition, the *Brassica* seeds demonstrate an altered fatty acid composition and yield a vegetable oil which has increased oleic acid content and decreased linoleic and linolenic acid content. Thus, the transformed seed can provide a source of carotenoid products as well as modified seed oil. In this manner, modified speciality oils can be produced and new sources of carotenoids for extraction and purification are provided.

The oils of the present invention also provide a substantial improvement with respect to stability as compared to two other major plant sources of carotenoids, marigold petals and red palm oil (mesocarp). Although instability is observed in seeds stored in air at room temperature as demonstrated by loss of approximately 20–30% of total carotenoids after 4 weeks of storage, the loss after 1–2 weeks is only 10%. Palm mesocarp, by contrast, must be processed within a day or two of harvest in order to avoid major losses of carotenoid. Furthermore, the carotenoid decomposition in the seeds of the present invention may be reduced significantly by storage of the seeds under nitrogen.

For the production of a seed having an increase in carotenoid biosynthesis, transformation of the plant with an early carotenoid biosynthesis gene is sufficient. By early carotenoid biosynthesis gene is intended geranylgeranyl pyrophosphate synthase, phytoene synthase, phytoene desaturase, and isopentenyl diphosphate (IPP) isomerase. A variety of sources are available for the early carotenoid biosynthesis genes and for the most part, a gene from any source can be utilized. However, it is recognized that because of co-suppression, the use of a plant gene native to the target host plant may not be desirable where increased expression of a particular enzyme is desired.

A number of early carotenoid biosynthesis genes have been isolated and are available for use in the methods of the present invention. See, for example:

IPP isomerase has been isolated from: *R. Capsulatus* (Hahn et al. (1996) *J. Bacteriol.* 178:619–624 and the references cited therein), GenBank Accession Nos. U48963 and X82627, *Clarkia xantiana* GenBank Accession No. U48962, *Arabidopsis thaliana* GenBank Accession No. U48961, *Schizosaccharmoyces pombe* GenBank Accession No. U21154, human GenBank Accession No. X17025, *Kluyveromyces lactis* GenBank Accession No. X14230;

geranylgeranyl pyrophosphate synthase from *E. Uredovora* Misawa et al. (1990) *J. Bacteriol.* 172:6704–6712 and Application WO 91/13078; and from plant sources, including white lupin (Aitken et al. (1995) *Plant Phys.* 108:837–838), bell pepper (Badillo et al. (1995) *Plant Mol. Biol.* 27:425–428) and Arabidopsis (Scolnik and Bartely (1994) *Plant Physiol* 104:1469–1470; Zhu et al. (1997) *Plant Cell Physiol.* 38:357–361).

phytoene synthase from a number of sources including *E. Uredovora, Rhodobacter capsulatus*, and plants Misawa et al. (1990) *J. Bacteriol.* 172:6704–6712, GenBank Accession No. D90087, Application WO 91/13078, Armstrong et al. (1989) *Mol. Gen. Genet.* 216:254–268, Armstrong, G. A. "Genetic Analysis and regulation of carotenoid biosynthesis. In R. C. Blankenship, M. T. Madigan, and C. E. Bauer (ed.), *Anoxygenic photosynthetic bacteria; advances in photosynthesis*. Kluwer Academic Publishers, Dordrecht, The Netherlands, Armstrong et al. (1990) *Proc. Natl. Acad Sci USA* 87:9975–9979, Armstrong et al. (1993) *Methods Enzymol.* 214:297–311, Bartley and Scolnik (1993) *J. Biol. Chem.* 268:27518–27521, Bartley et al. (1992) *J. Biol. Chem.* 267:5036–5039, Bramley et al. (1992) *Plant J.* 2:291–343, Ray et al. (1992) *Plant Mol. Biol.* 19:401–404, Ray et al. (1987) *Nucleic Acids Res.* 15:10587, Romer et al. (1994) *Biochem. Biophys. Res. Commun.* 196:1414–1421, Karvouni et al. (1995) *Plant Molecular Biology* 27:1153–1162, GenBank Accession Nos. U32636, Z37543, L37405, X95596, D58420, U32636, Z37543, X78814, X82458, S71770, L27652, L23424, X68017, L25812, M87280, M38424, X69172, X63873, and X60441, Armstrong, G. A. (1994) *J. Bacteriol.* 176:4795–4802 and the references cited therein; and, phytoene desaturase from bacterial sources including *E. uredovora* Misawa et al. (1990) *J. Bacteriol.* 172:6704–6712, and Application WO 91/13078 (GenBank Accession Nos. L37405, X95596, D58420, X82458, S71770, and M87280); and from plant sources, including maize (Li et al. (1996) *Plant Mol. Biol.* 30:269–279), tomato (Pecker et al. (1992) *Proc. Nat. Acad. Sci.* 89:4962–4966 and Aracri et al. (1994) *Plant Physiol.* 106:789), and *Capisum annuum* (bell beppers) (Hugueney et al. (1992) *J. Biochem.* 209: 399–407), GenBank Accession Nos. U37285, X59948, X78271, and X68058).

See, generally, Misawa et al. (1990) *J. of Bacteriology* 172:6704–6712, E.P. 0393690 B1, U.S. Pat. No. 5,429,939, Bartley et al. (1992) *J. Biol. Chem.* 267:5036–5039, Bird et al. (1991) *Biotechnology* 9:635–639, and U.S. Pat. No. 5,304,478, which disclosures are herein incorporated by reference.

Transformation with an early carotenoid gene, (referred to also as the primary gene), increases the biosynthetic activity of the carotenoid pathway, and can lead to increased production of particular carotenoids such as for example, α- and β-carotene. As described in more detail in the following examples, by expression of a phytoene synthase as the primary gene, large increases in the carotenoid content generally, and particularly in the levels of α- and β-carotene, are obtained in seeds of transformed plants. Oil comprising the carotenoids so produced may be extracted from the seeds to provide a valuable source of α- and β-carotenes. Such an oil may find use as a food colorant, for example to add color to margarines, or as a food oil. An edible food oil with high α- and β-carotene levels is of interest for prevention of Vitamin A deficiency which can result in night blindness. Thus, production of the transformed plants and extraction of the high α- and β-carotene oil to provide a useful food oil is particularly desirable in regions where night blindness is a widespread problem, such as in India and Asia.

In addition to the high high α- and β-carotene levels, levels of other carotenoids are also increased in the oils exemplified herein. For example, lutein levels are increased in seeds from plants transformed with a phytoene synthase gene, as well as in seeds from plants transformed with a GGPP synthase gene.

Furthermore, additional primary genes may be expressed to provide for even greater flux through the carotenoid pathway. For example, in the oilseed Brassica seeds containing the phytoene synthase gene as described herein, increased levels of phytoene are observed. Thus, increasing the expression of phytoene desaturase as well as the phytoene synthase may result in further increases in the levels of carotenoids, such as α- and β-carotene and lutein, produced. Furthermore, plants expressing both the phytoene synthase and the GGPP synthase genes are desirable and may be produced by crossing the 3390 and 3392 plants comprising these genes which are described herein.

In addition to the production of the carotenoids described herein, once the biosynthetic activity has been increased by expression of the primary carotenoid biosynthesis gene or genes, the pathway can be diverted for the production of specific compounds. The diversion involves the action of at least one second gene of interest, (the secondary gene). The secondary gene can encode an enzyme to force the production of a particular compound or alternatively can encode a gene to stop the pathway for the accumulation of a particular compound. For forcing the production of a particular compound, expression of a carotenoid biosynthesis gene in the pathway for the desired carotenoid compound is used. Genes native or foreign to the target plant host may find use in such methods, including, for example carotenoid biosynthesis genes from sources other than higher plant, such as bacteria, including Erwinia and Rhodobacter species. For stopping the pathway in order to accumulate a particular carotenoid compound, the secondary gene will provide for inhibition of transcription of a gene native to the target host plant, wherein the enzyme encoded by the inhibited gene is capable of modifying the desired carotenoid compound. Inhibition may be achieved by transcription of the native gene to be inhibited in either the sense (cosuppression) or antisense orientation of the gene.

For example, for alteration of the carotenoid composition towards the accumulation of higher levels of β-carotene derived carotenoids, such as zeaxanthin, zeaxanthin diglucoside, canthaxanthin, and astaxanthin, inhibition of lycopene epsilon cyclase is desired to prevent accumulation of alpha carotene and it's derivative carotenoids, such as lutein. In conjunction with the inhibition of lycopene epsilon cyclase, increased expression of a secondary gene may be desired for increased accumulation of a particular beta-carotene derived carotenoid. For example, increased β-carotene hydroxylase expression is useful for production of zeaxanthin, wherease increased β-carotene hydroxylase and keto-introducing enzyme expression is useful for production of astaxanthin. Alternatively, for accumulation of lycopene, inhibition of lycopene beta cyclase or of lycopene epsilon cyclase and lycopene beta cyclase is desired to reduce conversion of lycopene to alpha- and beta-carotene.

Secondary genes of interest in the present application include but are not limited to:

β-carotene hydroxylase or crtZ (Hundle et al. (1993) *FEBS Lett.* 315:329–334, GenBank Accession No. M87280) for the production of zeaxanthin;

genes encoding keto-introducing enzymes, such ascrtW (Misawa et al. (1995) *J. Bacteriol.* 177:6575–6584, WO 95/18220, WO 96/06172) or β-C-4-oxygenzse (crtO; Harker and Hirschberg (1997) *FEBS Lett.* 404:129–134) for the production of canthaxanthin;

crtZ and crtW or crtO for the production of astaxanthin;

ε-cyclase and ε-hydroxylase for the production of lutein;

ε-hydroxylase and crtZ for the production of lutein and zeaxanthin;

antisense lycopene ε-cyclase (GenBank Accession No. U50738) for increased production of β-carotene;

antisense lycopene ε-cyclase and lycopene β-cyclase (Hugueney et al. (1995) *Plant J.* 8:417–424, Cunningham F X Jr (1996) *Plant Cell* 8:1613–1626, Scolnik and Bartley (1995) *Plant Physiol.* 108:1343, GenBank Accession Nos. X86452, L40176, X81787, U50739 and X74599) for the production of lycopene;

antisense plant phytoene desaturase for the production of phytoene; etc.

In this manner, the pathway can be modified for the high production of any particular carotenoid compound of interest. Such compounds include but are not limited to α-cryptoxanthin, β-cryptoxanthin, ζ-carotene, phytofluene, neurosporane, and the like. Using the methods of the invention, any compound of interest in the carotenoid pathway can be produced at high levels in a seed.

The pathway can also be manipulated to decrease levels of a particular carotenoid by transformation of antisense DNA sequences which prevent the conversion of the presursor compound into the particular carotenoid being regulated.

Secondary genes can also be selected to alter the fatty acid content of the plant for the production of speciality oils. For example, acyl-ACP thioesterase genes having specificity for particular fatty acid chain lengths may be used. See, for example, U.S. Pat. No. 5,304,481, U.S. Pat. No. 5,455,167, WO 95/13390, WO 94/10288, WO 92/20236, WO 91/16421, WO 97/12047 and WO 96/36719. Other fatty acid biosynthesis genes of interest include, but are not limited to, β-keto acyl-ACP synthases (U.S. Pat. No. 5,510,255), fatty acyl CoA synthases (U.S. Pat. No. 5,455,947), fatty acyl reductases (U.S. Pat. No. 5,370,996) and stearoyl-ACP desaturases (WO 91/13972).

Of particular interest is the use of a mangosteen acyl-ACP thioesterase as a secondary gene for fatty acid content modification. As described in WO 96/36719 and WO 97/12047, a high stearate content may be obtained in seeds by expression of a mangosteen acyl-ACP thioesterase. To combine the high oleic acid trait of the 3390 plants described herein with the 5266 high stearate plants described in WO 97/12047, crosses were made between 3390-1 and 5266-35 and between 3390-1 and 5266-5. Seeds resulting from these crosses contained oil having a high stearate, low linoleic, low linolenic and high carotenoid phenotype.

Any means for producing a plant comprising the primary gene or both the primary and secondary genes are encompassed by the present invention. For example, the secondary gene of interest can be used to transform a plant at the same time as the primary gene (cotransformation), the secondary gene can be introduced into a plant which has already been transformed with the primary gene, or alternatively, transformed plants, one expressing the primary gene and one expressing the secondary gene, can be crossed to bring the genes together in the same plant.

By combining the genes with tissue specific promoters, the carotenoid levels can be altered in particular tissues of the plant. Thus, carotenoid levels in the seed, including embryos and endosperm, can be altered by the use of seed specific transcriptional initiation regions. Such regions are disclosed, for example, in U.S. Pat. No. 5,420,034, which disclosure is herein incorporated by reference.

In this manner, the transformed seed provides a factory for the production of modified oils. The modified oil may be used or alternatively, the compounds in the oils can be isolated. Thus, the present invention allows for the production of particular compounds of interest as well as speciality oils.

The primary or secondary genes encoding the enzymes of interest can be used in expression cassettes for expression in the transformed plant tissues. To alter the carotenoid or fatty acid levels in a plant of interest, the plant is transformed with at least one expression cassette comprising a transcriptional initiation region linked to a gene of interest. Such an expression cassette is provided with a plurality of restriction sites for insertion of the gene of interest to be under the transcriptional regulation of the regulatory regions.

The transcriptional initiation may be native or analogous to the host or foreign or heterologous to the host. By foreign is intended that the transcriptional initiation region is not found the wild-type host into which the transcriptional initiation region is introduced.

Of particular interest are those transcriptional initiation regions associated with storage proteins, such as napin, cruciferin, β-conglycinin, phaseolin, or the like, and proteins involved in fatty acid biosynthesis, such as acyl carrier protein (ACP). See, U.S. Pat. No. 5,420,034, herein incorporated by reference.

The transcriptional cassette will include the in 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al., (1991), *Mol. Gen. Genet.*, 262:141–144; Proudfoot, (1991), *Cell*, 64:671–674; Sanfacon et al., (1991), *Genes Dev.*, 5:141–149; Mogen et al., (1990), *Plant Cell*, 2:1261–1272; Munroe et al., (1990), *Gene*, 91:151–158; Ballas et al., (1989), *Nucleic Acids Res.*, 17:7891–7903; Joshi et al., (1987), *Nucleic Acid Res.*, 15:9627–9639).

For the most part, the genes of interest of the present invention will be targeted to plastids, such as chloroplasts, for expression. In this manner, where the gene of interest is not directly inserted into the plastid, the expression cassette will additionally contain a gene encoding a transit peptide to direct the gene of interest to the plastid. Such transit peptides are known in the art. See, for example, Von Heijne et al. (1991) *Plant Mol. Biol. Rep.* 9:104–126; Clark et al. (1989) *J. Biol Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481. Plant carotenoid genes useful in the invention may utilize native or heterologous transit peptides.

It is noted that where the gene or DNA sequence of interest is an antisense DNA, targeting to a plastid is not required.

The construct may also include any other necessary regulators such as plant translational consensus sequences (Joshi, C. P., (1987), *Nucleic Acids Research*, 15:6643–6653), introns (Luehrsen and Walbot, (1991), *Mol. Gen. Genet.*, 225:81–93) and the like, operably linked to the nucleotide sequence of interest.

It may be beneficial to include 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA* 86:6126–6130); potyvirus leaders, for example, TEV leader (Tobacco Etch Virus) (Allison et al., (1986); MDMV leader (Maize Dwarf Mosaic Virus); *Virology*, 154:9–20), and human immunoglobulin heavy-chain binding protein (BiP), (Macejak, D. G., and Sarnow, P., (1991), *Nature*, 353:90–94; untranslated leader from the coat protein mRNA of alfalfa mosaic virus (AMV RNA 4), (Jobling, S. A., and Gehrke, L., (1987), *Nature*, 325:622–625; tobacco mosaic virus leader (TMV), (Gallie, D. R. et al., (1989), *Molecular Biology of RNA*, pages 237–256; and maize chlorotic mottle virus leader (MCMV) (Lommel, S. A. et al., (1991), *Virology*, 81:382–385. See also, Della-Cioppa et al., (1987), *Plant Physiology*, 84:965–968.

Depending upon where the DNA sequence of interest is to be expressed, it may be desirable to synthesize the sequence with plant preferred codons, or alternatively with chloroplast preferred codons. The plant preferred codons may be determined from the codons of highest frequency in the proteins expressed in the largest amount in the particular plant species of interest. See, EPA 0359472; EPA 0385962; WO 91/16432; Perlak et al. (1991) *Proc. Natl. Acad. Sci. USA* 88:3324–3328; and Murray et al. (1989) *Nucleic Acids Research* 17: 477–498. In this manner, the nucleotide sequences can be optimized for expression in any plant. It is recognized that all or any part of the gene sequence may be optimized or synthetic. That is, synthetic or partially optimized sequences may also be used. For the construction of chloroplast preferred genes, see U.S. Pat. No. 5,545,817.

In preparing the transcription cassette, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

The recombinant DNA molecules of the invention can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al. (1986) *BioTechniques* 4:320–334), electroporation (Riggs et al. (1986) *Proc. Natl. Acad. Sci. USA* 83:5602–5606, *Agrobacterium* mediated transformation (Hinchee et al. (1988) *Biotechnology* 6:915–921) and ballistic particle acceleration (see, for example, Sanford et al., U.S. Pat. No. 4,945,050; and McCabe et al. (1988) *Biotechnology* 6:923–926). Also see, Weissinger et al. (1988) *Annual Rev. Genet.* 22:421–477; Sanford et al. (1987) *Particulate Science and Technology* 5:27–37(onion); Christou et al. (1988) *Plant Physiol.* 87:671–674(soybean); McCabe et al. (1988) *Bio/Technology* 6:923–926 (soybean); Datta et al. (1990) *Biotechnology* 8:736–740(rice); Klein et al. (1988) *Proc. Natl. Acad. Sci. USA*, 85:4305–4309(maize); Klein et al. (1988) *Biotechnology* 6:559–563 (maize); Klein et al. (1988) *Plant Physiol.* 91:440–444(maize); Fromm et al. (1990) *Biotechnology* 8:833–839; and Gordon-Kamm et al. (1990) *Plant Cell* 2:603–618 (maize).

Alternatively, a plant plastid can be transformed directly. Stable transformation of chloroplasts has been reported in higher plants, see, for example, SVAB et al. (1990) *Proc. Nat'l. Acad. Sci. USA* 87:8526–8530; SVAB & Maliga (1993) *Proc. Nat'l Acad. Sci. USA* 90:913–917; Staub & Maliga (1993) *Embo J.* 12:601–606. The method relies on particle gun delivery of DNA containing a selectable marker and targeting of the DNA to the plastid genome through homologous recombination. In such methods, plastid gene expression can be accomplished by use of a plastid gene promoter or by trans-activation of a silent plastid-borne transgene positioned for expression from a selective promoter sequence such as that recognized by T7 RNA polymerase. The silent plastid gene is activated by expression of the specific RNA polymerase from a nuclear expression construct and targeting of the polymerase to the plastid by use of a transit peptide. Tissue-specific expression may be obtained in such a method by use of a nuclear-encoded and plastid-directed specific RNA polymerase expressed from a suitable plant tissue specific promoter. Such a system has been reported in McBride et al. (1994) *Proc. Natl. Acad. Sci., USA* 91:7301–7305.

The cells which have been transformed may be grown into plants in accordance with conventional ways. See, for example, McCormick et al., *Plant Cell Reports* (1986), 5:81–84. These plants may then be grown, and either pollinated with the same transformed strainer or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

As a host cell, any plant variety may be employed. Of particular interest, are plant species which provide seeds of interest. For the most part, plants will be chosen where the seed is produced in high amounts, a seed-specific product of interest is involved, or the seed or a seed part is edible. Seeds of interest include the oil seeds, such as oilseed Brassica seeds, cotton seeds, soybean, safflower, sunflower, coconut, palm, and the like; grain seeds, e.g. wheat, barley, oats, amaranth, flax, rye, triticale, rice, corn, etc.; other edible seeds or seeds with edible parts including pumpkin, squash, sesame, poppy, grape, mung beans, peanut, peas, beans, radish, alfalfa, cocoa, coffee, tree nuts such as walnuts, almonds, pecans, chick-peas etc.

In one embodiment of the invention, seed transcriptional initiation regions are used in combination with at least one carotenoid biosynthesis gene. This increases the activity of the carotenoid pathway and alters carotenoid levels in the transformed seed. In this manner, particular genes can be selected to promote the formation of compounds of interest. Where the gene selected is an early carotenoid biosynthesis gene the transformed seed has a significant increase in carotenoid biosynthesis as the result of an increase in the flux through the pathway. For *Brassica* seeds transformed with an early carotenoid biosynthesis gene, significant increases in the production of $\alpha$-carotene, $\beta$-carotene and smaller increases in lutein in the seed oil, as well as altered oil fatty acid compositions are obtained.

Where the early carotenoid biosynthesis gene is phytoene synthase, significant increases of a particular carotenoid include those ranging from a 10 to a 50 fold increase, preferably at least a 50 to a 100 fold increase, more preferably, at least a 50 to a 200 fold increase, such as the increases seen in $\alpha$-carotene and $\beta$-carotene levels. Lutein levels, in this case, are also increased, but lower increases of 1.5–2 fold are obtained. At the same time, total carotenoid levels may be increased at least 10 to 25 fold, preferably 25 to 60 fold, and more preferably 25 to 100 fold. Thus, a seed of the invention transformed with a phytoene synthase gene has a substantial increase in levels of $\alpha$- and $\beta$-carotene and total carotenoids, as well as smaller increases in lutein and other carotenoids. In some cases, it is not possible to quantitate the fold increase in a given carotenoid compound, as the levels are too low to detect in seeds from non-transformed. In *Brassica napus*, for example, $\alpha$-cyptoxanthin, lycopene, phytoene and phytofluene are all detected in various levels in seeds transformed with a crtB gene, but are not detectable in seeds from untransformed *Brassica napus* plants.

Where the early carotenoid biosynthesis gene is GGPP synthase, 1.5 to 2 fold increases in lutein and $\beta$-carotene may be obtained. Lycopene is also detected in seeds from *Brassica napus* plants transformed with a crtE (GGPP synthase) gene. Total carotenoids in this case are also increased approximately 2 fold. Thus, also of interest as sources of carotenoids are plants which have been engineered to express increased levels of both phytoene synthase and GGPP synthase.

This metabolic energy effected by transformation with an early carotenoid gene can be funneled into a metabolic compound of choice by transformation with a second gene. As discussed above, the second gene is designed to promote the synthesis of a particular carotenoid by promoting the formation of the carotenoid of interest or alternatively by stopping the pathway to allow for the buildup of compounds. Therefore, significant amounts of carotenoids of interest can be produced in the transformed seeds of the present invention.

The seeds of the invention which have been transformed with the primary early carotenoid biosynthesis gene also provide a source for novel oil compositions. The use of phytoene synthase as the primary gene, for example, results in substantial increases in oleic acid content in seed oil. By substantial increase is intended an increase of from about 5% to about 40%, specifically from about 20% to about 40%, more specifically from about 30% to about 40%. Thus, the seeds of the invention which have been transformed with a primary early carotenoid biosynthesis gene provide a source for modified oils having a high oleic acid content. That is, carotenoid biosynthesis genes, particularly early carotenoid biosynthesis genes can be used to produce seeds having at least 70% oleic acid, on a weight percentage basis. The oleic acid content in any seed can be altered by the present methods, even those seeds having a naturally high oleic acid content. Alteration of seeds having naturally high oleic acid contents by the present methods can result in total oleic acid contents of as high as 80%.

Importantly, there is also a decrease in linoleic and linolenic acid content. By decrease in linoleic fatty acid content is intended a decrease from about 10% to about 25%, preferably about 25% to about 40%, more preferably about 35% to about 60%. By decrease in linolenic fatty acid content is intended a decrease from about 10% to about 30%, preferably about 30% to about 60%, more preferably about 50% to about 75%. Thus, the methods of the invention result in oils which are more oxidatively stable than the naturally occurring oils. The modified oils of the invention are low-saturate, high oleic and low linolenic. Furthermore, the present invention provides oils high in monounsaturated fatty acids which are important as a dietary constituent.

Based on the methods disclosed herein, seed oil can be modified to engineer an oil with a high oleic acid content as well as a high level of a carotenoid of interest. High oleic acid and and high $\alpha$- and $\beta$-carotene oils would have a longer shelf life as both the oleic acid and $\alpha$- and $\beta$-carotene content would lend stability. It is also noted that such oils are more desirable as sources of carotenoids than the natural red palm oil, which oil contains high levels of saturated fatty acids.

The transformed seed of the invention can thus provide a source of carotenoid products as well as modified fatty acids. Where the intent is to produce particular carotenoid compounds of interest, methods are available in the art for the purification of the carotenoid compounds. In the same manner, methods available in the art can be utilized to produce oils purified of carotenoids. See, generally, WO 96/13149 and Favati et al. (1988) *J. Food Sci.* 53:1532 and the references cited therein.

In addition to altering the carotenoid levels in seeds, the tocopherol levels can be altered, preferably increased. Such seeds with increased levels of tocopherol, particularly α-tocopherol, are desirable as α-tocopherol is the most important form of the vitamin E family. Vitamin E is essential for the nutrition of humans and other animals. Evidence is available that vitamin E functions in the body in maintaining the integrity of the red blood cells, as essential in cellular respiration, is involved in the biosynthesis of DNA, and acts as an antioxidant which may have implications in protecting cells from carcinogens. Thus, seeds and oils having increased tocopherol levels are desirable. Oils having a nearly 50% increase in α-tocopherol levels are provided herein, and seed oils having even greater increases, up to 2–5 fold, are envisioned using the methods of the present invention.

The transformed seed and embryos additionally find use as screenable markers. That is, transformed seed and embryos can be visually determined and selected based on color as a result of the increased carotenoid content. The transformed seeds or embryos display a color ranging from yellow to orange to red as a result of the increased carotenoid levels. Therefore, where plant transformation methods involve an embryonic stage, such as in transformation of cotton or soybean, the carotenoid gene can be used in plant transformation experiments as a marker gene to allow for visual selection of transformants. Likewise, segregating seed can easily be identified as described further in the following examples.

The following examples are offered by way of illustration and not by way of limitation.

EXPERIMENTAL

EXAMPLE 1

Expression Construct and Plant Transformation
A. SSU Fusions to *E. uredovora* Carotenoid Biosynthesis Genes
(1) Phytoene Synthase The SSU leader and crtB gene sequences were joined by PCR. The sequence of the SSU/crtB fusion is shown in FIG. 1. The crtB gene from nucleotides 5057 to 5363 (numbering according to Misawa et al. (1990) supra) was joined to the SSU leader as follows. A BglII site was included upstream of the SSU leader start site to facilitate cloning. The thymidine nucleotide at 5057 of crtB was changed to an adenosine to make the first amino acid at the SSU leader/crtB junction a methionine, and the splice site a cys-met-asn. The native splice site for SSU is csy-met-gln. Note that Misawa et al. (1990) supra) indicates that the start site for the coding region for crtB is at nucleotide 5096. Thus, there are 13 amino acids upstream of the published start of the coding region for crtB and after the SSU splice site in the crtB/SSU fusion. Twelve of these amino acids are translated from *Erwinia* crtB upstream sequence and one is the added methionine. The crtB from 5363 (EcoRV) to 6009 (EcoRI) was then attached to the SSU-crtB fusion to obtain a complete SSU-crtB fusion construct designated pCGN3373 (FIG. 1).

(2) Phytoene Desaturase

A plasmid comprising a *E. uredovora* crtI gene fused to the transit peptide sequence of the pea Rubisco small subunit was described by Misawa et al. (*The Plant Journal* (1993) 4:833–840. An approximately 2.1 kb XbaI/EcoRI fragment of this plasmid containing the SSU-crtI fusion and a nos 3' termination region was cloned in position for expression from a napin 5' promoter.

(3) GGPP Synthase

A similar construct containing the SSU transit fused to an *E. uredovora* crtE gene was obtained. The SSU-crtE fusion is present on an approximately 1.2 kb BglII/BamHI fragment in pCGN3360.

B. Expression Constructs for Plant Transformation
(1) Phytoene Synthase pCGN3373 carrying the complete SSU/crtB fusion was cut with BglII and BamHI to excise the SSU/crtB fusion. The resulting fragment was ligated into the napin expression cassette in pCGN3223 at the BamHI site (see WO 94/10288 for description of napin expression cassette). The resulting construct, pCGN3389, was digested with HindIII to excise the napin 5'-SSU/crtB-napin 3' fragment, which was then cloned into HindIII cut pCGN1559PASS yielding pCGN3390. pCGN1559PASS is a binary vector for *Agrobacterium*-mediated transformation such as those described by McBride et al. (*Plant Mol Biol.* (1990) 14:269–276) and is prepared from pCGN1559 by substitution of the pCGN1559 linker region with a linker region containing the following restriction digestion sites: Asp718/AscI/PacI/XbaI/BamHI/SwaI/Sse8387(PstI)/HindIII. A map of pCGN3390 is provided in FIG. 2A.

(2) Phytoene Desaturase

Figure 2B:
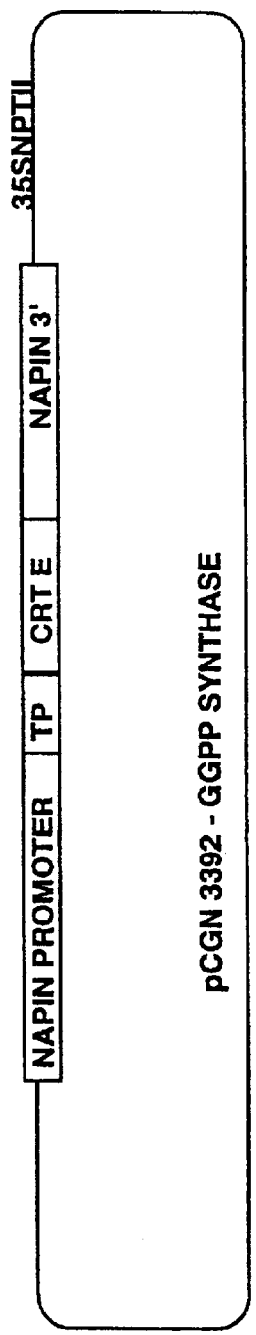
FIG. 2B shows plasmid pCGN3392which contains the napin promoter operably linked to the SSU/crtE sequence.
Figure 2C:
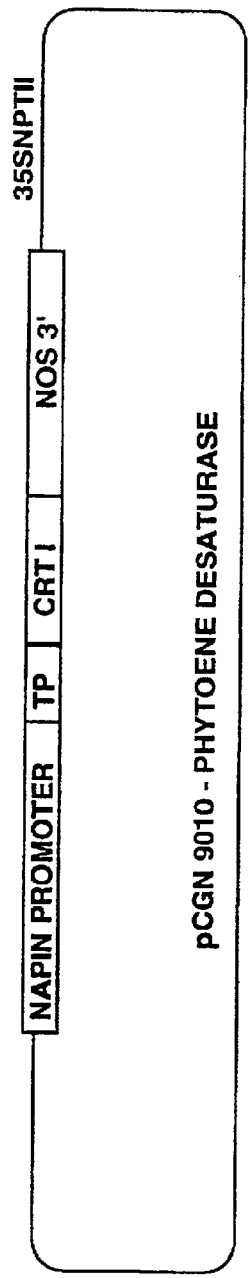
FIG. 2C shows plasmid pCGN9010 which contains the napin promoter operably linked to the SSU/crtI sequence.

A fragment comprising a napin 5'/SSU-crtI fusion/nos 3' construct as described above was cloned into a binary vector for plant transformation resulting in pCGN9010. A map of pCGN9010 is provided in FIG. 2C.

(3) GGPP Synthase pCGN3360 carrying the complete SSU/crtE fusion was cut with BglII and BamHI to excise the SSU/crtE fusion. The resulting 1.2 kb fragment was ligated into the napin expression cassette in pCGN3223 at the BamHI site. The resulting construct, pCGN3391, was digested with HindIII to excise the napin promoter-SSU/crtE napin 3' fragment, which was then cloned into HindIII cut pCGN1559PASS yielding pCGN3392. A map of pCGN3392 is provided in FIG. 2B.

(4) Phytoene Synthase+Phytoene Desaturase

Figure 2D:
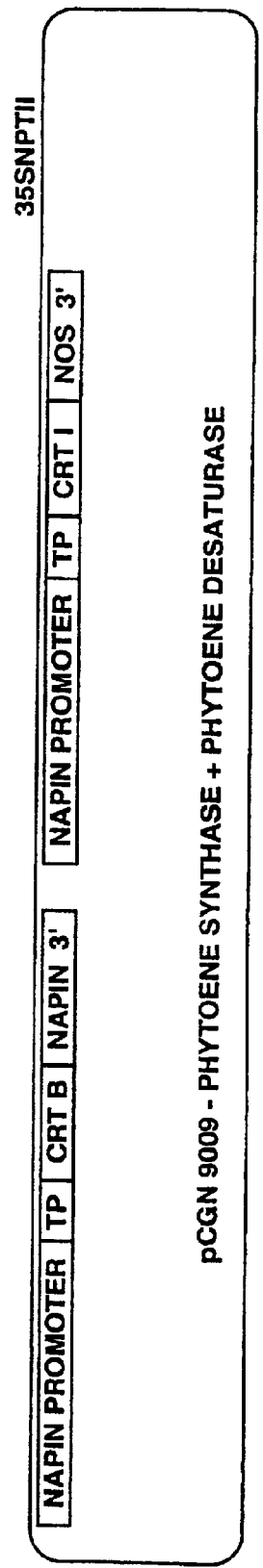
FIG. 2D shows plasmid pCGN9009 which contains the napin promoter operably linked to the SSU/crtB sequence and the napin promoter operably linked to the SSU/crtI sequence.

The napin 5'-SSU/crtB-napin 3' fragment from pCGN3389 and the napin 5'/SSU-crtI fusion/nos 3' as present in pCGN9010 were inserted into a binary vector resulting in pCGN9009, shown in FIG. 2D.

(5) Antisense Epsilon Cyclase+Phytoene Synthase

Figure 9:
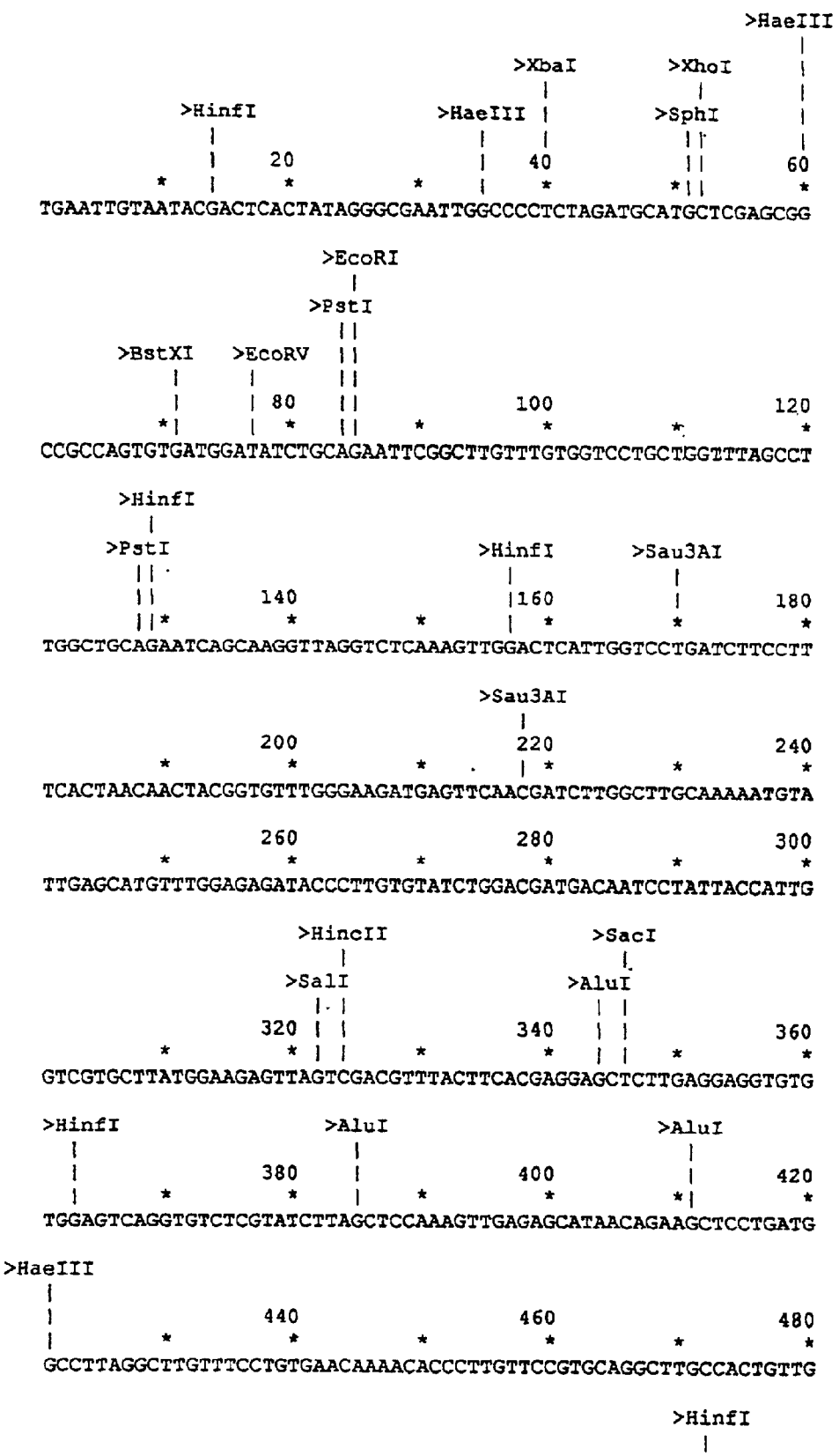
FIG. 9 provides sequence (SEQ ID NO: 2) of *B. napus* epsilon cyclase cDNA clone 9–4.
Figure 10:
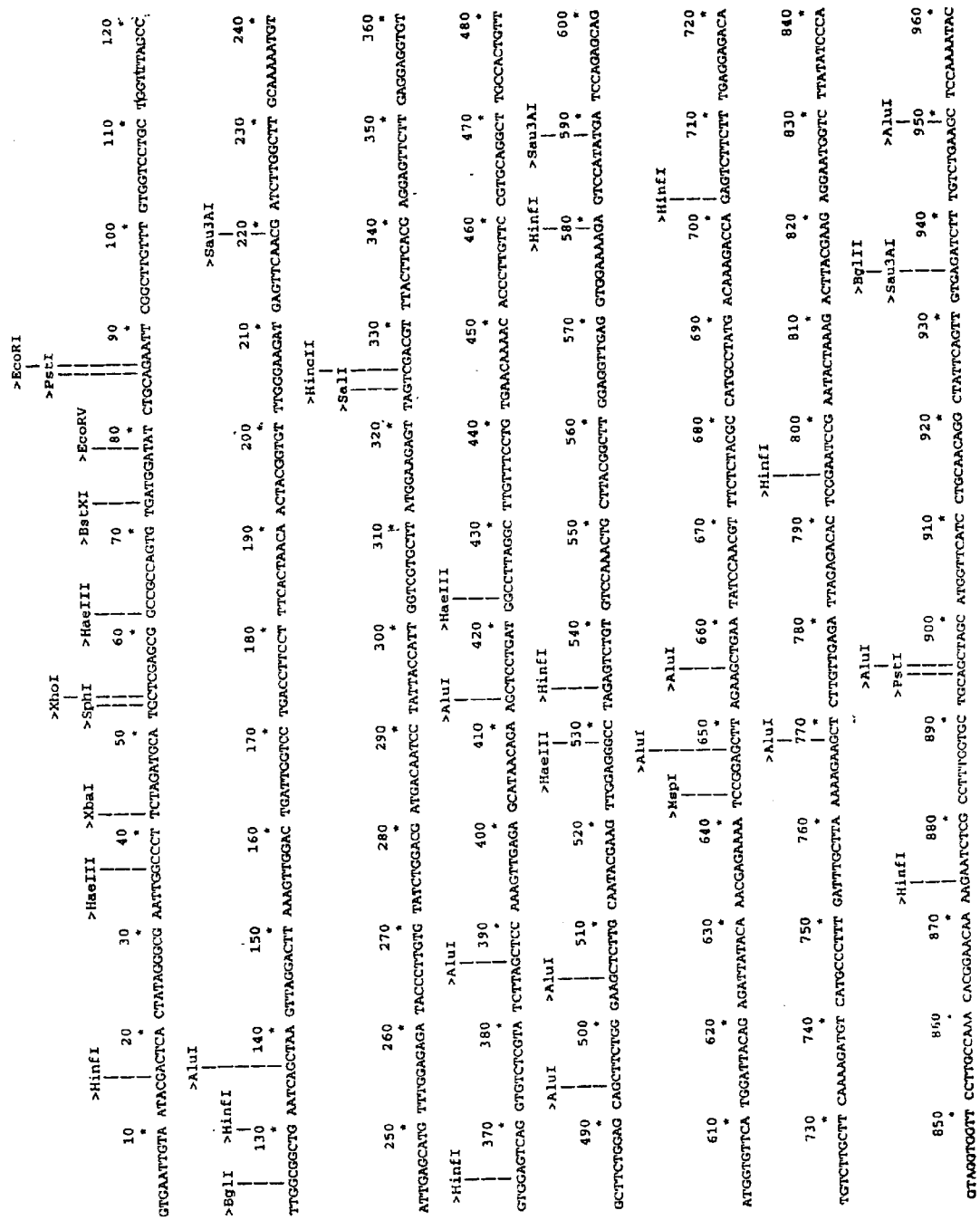
FIG. 10 provides sequence (SEQ ID NO: 3) of *B. napus* epsilon cyclase cDNA clone 7–6.

*Brassica napus* epsilon cyclase genes are isolated by PCR using primers designed from an *Arabidopsis* epsilon cyclase gene (Cunningham F X Jr (1996) *Plant Cell* 8:1613–1626). Sequence of *B. napus* epsilon cyclase genes is provided in FIGS. 9 (clone 9-4) and 10 (clone 7-6). An antisense construct is prepared by cloning anXhoI/BamHI fragment of cDNA clone 9-4 into a napin expression cassette (pCGN3223) digested with XhoI and BglII. The napin 5'-antisense epsilon cyclase-napin 3' fragment is cloned along with a napin 5'-SSU/crtB-napin 3' fragment, fragment into a binary vector for plant transformation, resulting in pCGN9002, shown in FIG. 2E.

(6) Antisense Beta Cyclase+Phytoene Synthase

*Brassica napus* beta cyclase genes are isolated by PCR using primers designed from an *Arabidopsis* beta cyclase gene (Cunningham F X Jr (1996) *Plant Cell* 8:1613–1626). Sequence of a *B. napus* beta cyclase cDNA, 32-3, is provided in FIG. 11. An antisense construct is prepared by cloning anXhoI fragment of the beta cyclase cDNA clone into a napin expression cassette (pCGN3223) digested with XhoI. A clone containing the beta cyclase in the antisense orientation is selected. The napin 5'-antisense beta cyclase-napin 3' fragment is cloned along with a napin 5'-SSU/crtB-napin 3' fragment into a binary vector for plant transformation, resulting in pCGN9017, shown in FIG. 2F.

C. Plant Transformation

Transformed *Brassica napus* plants containing the above described constructs are obtained as described in Radke et al. (*Theor. Appl. Genet.* (1988) 75:685–694 and *Plant Cell Reports* (1992) 11:499–505).

EXAMPLE 2

Analysis of Transgenic Plants

A. Visual Observations and Segregation Ratios

The napin-SSU leader/crtB plants in 212/86 were tagged at 21 days, 28 days and 35 days post anthesis. When the first plant, 3390-1 was harvested at 28 days, some of the seeds were obviously orange. AT 35 dpa, the orange was obvious enough that a segregation ratio could be obtained. This trend of orange seeds has continued and is seen in each of the 17 lines harvested that have been obtained. A table of the segregation ratios is included below in Table 1.

TABLE 1

| Generation | Plant # | Orange | Green | Ratio | Chi Square |
|---|---|---|---|---|---|
| T2 | 3390-1 | 291 | 88 | 3 to 1 | 0.64 |
| T2 | 3390-2 | 150 | 22 | No fit | |
| T2 | 3390-8 | 293 | 87 | 3 to 1 | 0.90 |
| T2 | 3390-4 | 277 | 82 | 3 to 1 | 0.89 |
| T2 | 3390-5 | 243 | 62 | 3 to 1 | 1.90 |
| T2 | 3390-7 | 236 | 89 | 3 to 1 | 0.99 |
| T2 | 3390-6 | 307 | 5 | 63 to 1 | 0.00 |
| T2 | 3390-3 | 121 | 50 | No fit | 1.64 |
| T2 | 3390-11 | 294 | 105 | 3 to 1 | 0.37 |
| T2 | 3390-15 | 287 | 83 | 3 to 1 | 1.30 |
| T2 | 3390-16 | 187 | 65 | 3 to 1 | 0.08 |
| T2 | 3390-17 | 105 | 104 | No fit | |
| T2 | 3390-12 | 119 | 28 | 3 to 1 | 2.78 |
| T2 | 3390-14 | 283 | 107 | 3 to 1 | 1.23 |
| T2 | 3390-19 | 238 | 94 | 3 to 1 | 1.94 |
| T2 | 3390-20 | 251 | 4 | 63 to 1 | 0.00 |
| T2 | 3390-27 | 229 | 4 | 63 to 1 | 0.04 |

B. Carotenoid Analysis of Developing Seeds

Carotenoids were extracted from seeds harvested at approximately 35 days post-anthesis as follows. Eight seed samples of orange seeds from transgenic plant 3390-1 and eight seed samples of a 212/86 variety rapeseed control plant were ground in 200 µl of 70% acetone/30% methanol. The ground seed mixture was then spun in a microcentrifuge for approximately 5 minutes and the supernatant removed. Two additional 70% acetone/30% methanol extractions were conducted with the pelleted seed material and all three supernatants pooled and labeled A/M extract.

At this point in the extraction, the control seed pellets are white, whereas the seed pellets from the transgenic seeds have a yellow color. The pellets are then extracted twice with ether and the resultant supernatants pooled and labeled E extract. The A/M extract was then transferred to ether as follows. 450 µl ether and 600 µl of water were added to the extracts, followed by removal of the ether layers. The A/M extracts were then washed two more time with 400 µl of ether, and the ether fractions from the three A/M washes pooled. The E extracts described above were washed once with 400 µl of water and pooled with the A/M ether fractions. The pooled ether fractions were blown down to a volume of approximately 300 µl with nitrogen gas and filtered using a syringe microfilter. The sample vials were rinsed with approximately 100 µl ether and the rinse was similarly filtered and pooled with the initial filtrate, yielding total volume of approximately 150 µl. A 50 µl aliquot was stored at −20γC until further analysis and the remaining 100 µl sample was saponified as follows. 100 µl of 10% potassium hydroxide (KOH) in methanol was added to each 100 µl sample and the mixture stored in the dark at room temperature for approximately 2 hours. 400 µl of water was then added to the samples and the ether phase removed. For better phase separation, saturated NaCl may be substituted for the water. The water solution was then extracted twice more with 100 µl of ether and the ether samples pooled and washed with water.

The saponified samples were then analyzed by HPLC analysis on a Rainin microsorb C18 column (25 cm length, 4.6 mm outside diameter) at a flow rate of 1.5 ml per minute. The gradient used for elution is as follows:

A=acetonitrile
B=hexane/methylene chloride (1:1)
C=methanol.

The initial solution was 70:20:10 (A:B:C). At 2.5 minutes the solution is ramped over 5 minutes to 65:25:10 (A:B:C) and held at this for 12.5 minutes. The solution is then ramped to 70:20:10 (A:B:C) over two minutes followed by a three minute delay prior to injection of the next sample. The absorbance of the eluting samples is continuously monitored at 450 and 280 nm and known chemical and biological standards were used to identify the various absorbance peaks.

Figure 3:
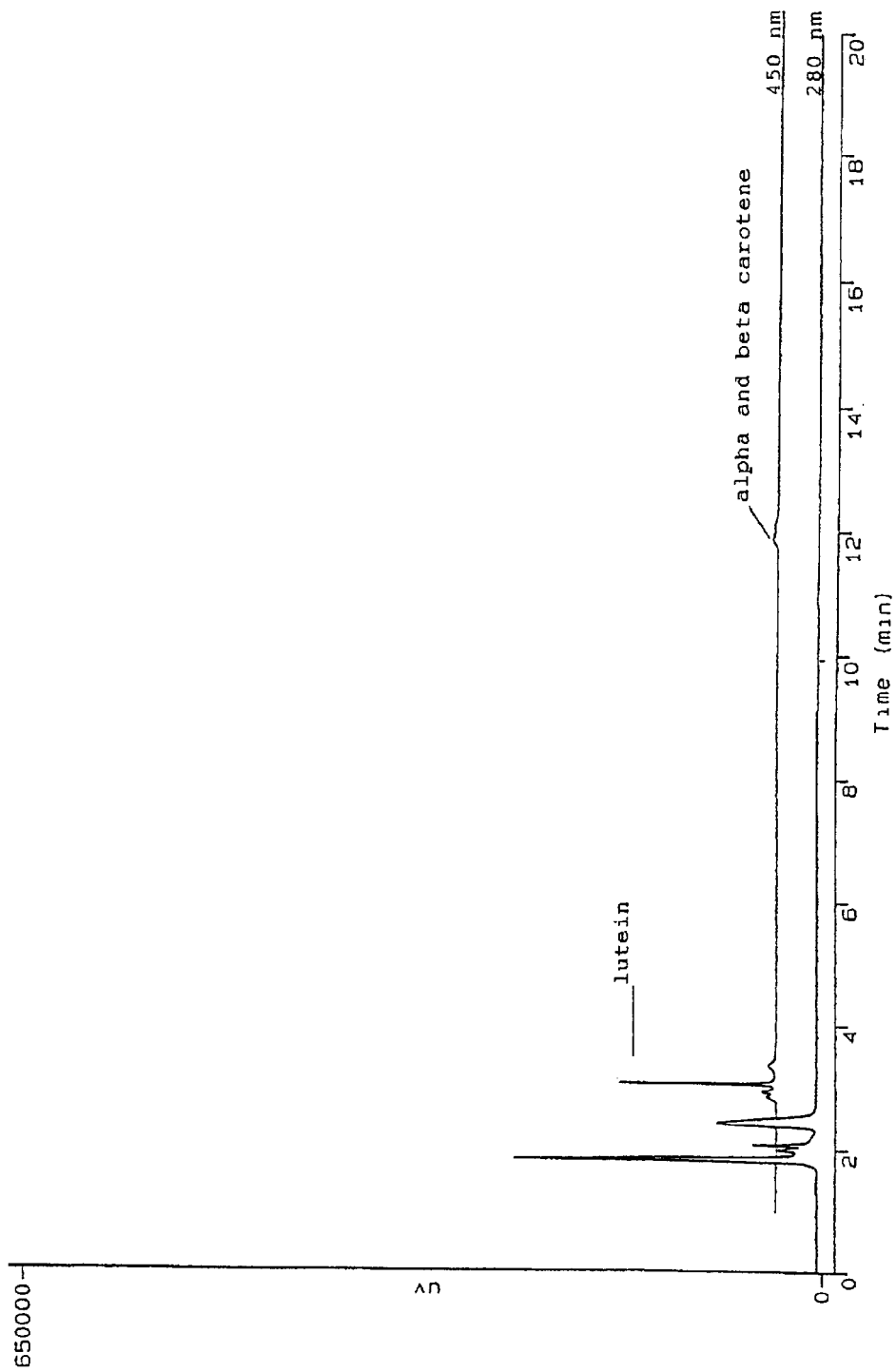
FIG. 3 shows the results of analyses of saponified samples for control seeds.
Figure 4:
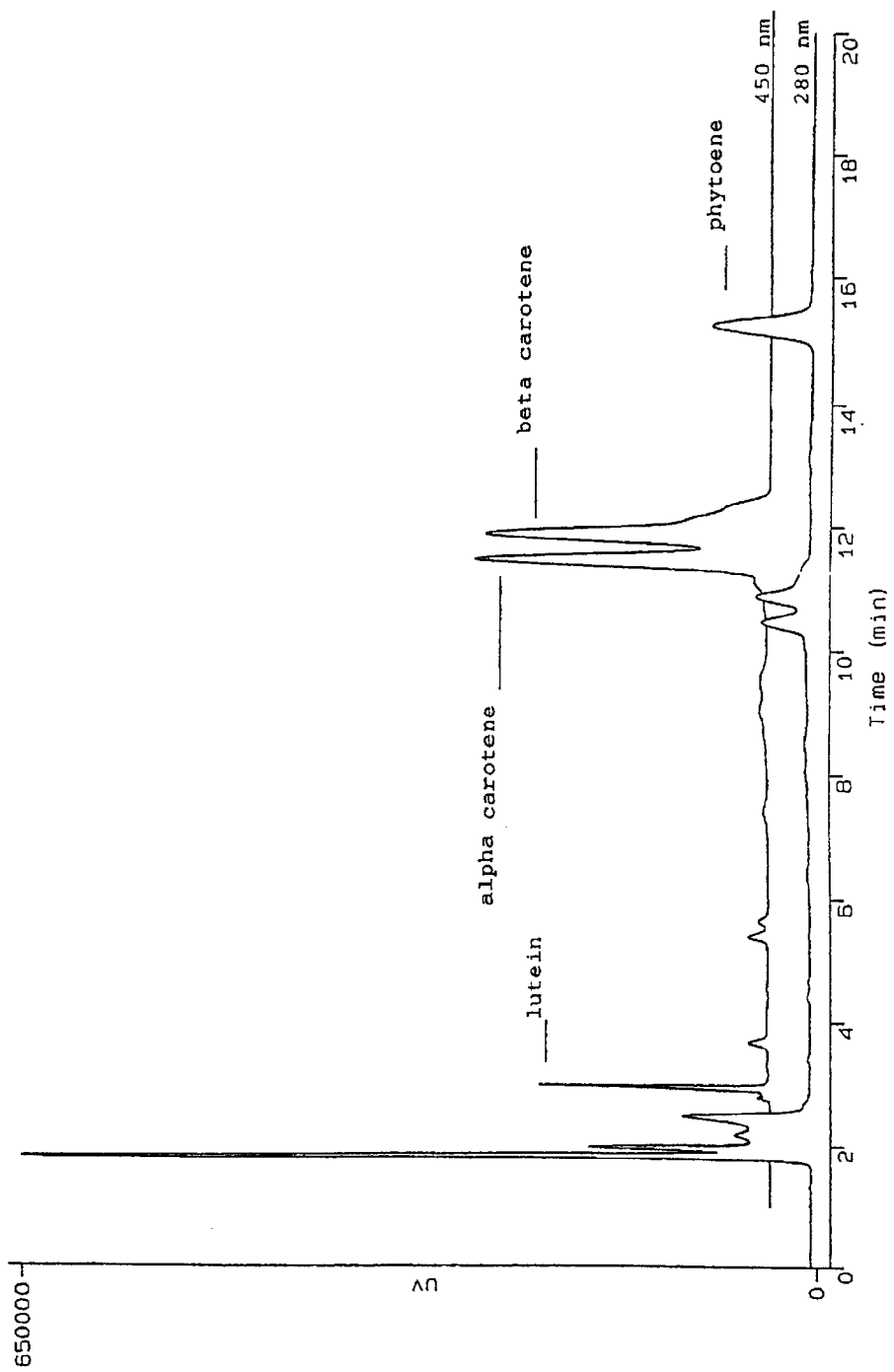
FIG. 4 shows the results of analyses of saponified samples for pCGN3390 transformed seeds.

In FIGS. 3 and 4, results of analyses of saponified samples are provided for control and pCGN3390 transformed seeds, respectively. Clear increases in the levels of α- and β-carotene and phytoene in the transagenic plant seeds are observed, as well as smaller increases in levels of the hydroxylated carotenoid, lutein.

C. Carotenoid and Tocopherol Analysis of Mature Seeds from crtB Transgenic Plants Mature 3390 T2 seed were sent to an analytical laboratory for quantitative analysis using standard HPLC methods known in the art. These results of these analysis are shown in Table 2 below. Compound levels are presented as µg/g.

Seeds designated "Maroon" were selected based on seed color. The seeds which have orange embryos appear maroon colored at maturity as opposed to the black-brown appearance of seeds from wild type plants of this cultivar. Seeds designated as "Random" were not selected for color. As 3390-1 is segregating 3 to 1 for Kan, the "Random" population includes a proportion of nulls. The maroon population contains only transgenics. Due to an effort to exclude nulls from this population, the inclusion of homozygotes may be favored.

TABLE 2

| COMPOUND | CONTROL | 3390-1 RANDOM | 3390-1 MAROON |
|---|---|---|---|
| Lutein | 7.2 | 18 | 26 |
| Zeaxanthin | nd* | nd | nd |
| α-cryptoxanthin | nd | 8 | 15 |
| β-cryptoxanthin | nd | nd | nd |
| Lycopene | nd | 2.3 | 5.1 |
| cis-Lycopene | nd | 2.9 | 5.4 |
| α-carotene | 0.6 | 124 | 244 |
| β-carotene | 0.9 | 177 | 338 |
| cis-β-carotene | 0.2 | 12 | 26 |
| Other | 6 | 34 | 51 |
| Total colored carotenoids | 14.9 | 378.2 | 710.5 |

TABLE 2-continued

| COMPOUND | CONTROL | 3390-1 RANDOM | 3390-1 MAROON |
|---|---|---|---|
| Phytoene | nd | 62 | 139 |
| Phytofluene | nd | 24 | 54 |
| Total all carotenoids | 14.9 | 464.2 | 903.5 |
| Alpha-tocopherol | 74 | 93 | 109 |
| Gamma-tocopherol | 246 | 188 | 95 |
| Delta-tocopherol | 3 | 5 | 5 |

*nd = not detected

In the non-transgenic sample, "other" includes mostly very polar compounds, such as neoxanthin, violaxanthin, etc. In the transgenic sample "other" includes these and additional compounds, such as zeta-carotene, neurosporene, and mono-cyclic carotenoids.

Results of carotenoid analysis of 3390 T2 seeds from transformed plants of *B. napus* variety Quantum (SP30021) are presented in FIG. 12.

Results of carotenoid analysis of 3390 T3 seeds from transformed plants of *B. napus* variety 212/86 (SP001) are presented in FIG. 13.

The above results demonstrate that α- and β-carotenes levels are significantly increased in the mature seeds as the result of expression of the crtB gene. Generally, the overall increase in carotenoids is quite high, nearly 50 fold for colored carotenoids and up to 60 fold if phytoene and phytofluene are included. It is clear that the flux through the isoprenoid pathway has been dramatically increased. Additionally it is noted that the α-tocopherol (Vitamin E) levels are also increased by nearly 50%.

D. Germination Studies

Ten mature seeds of 3390-1 and 10 seeds of 212/86 control were planted in soil and grown in a walk-in growth chamber. The transgenics emerged 1 to 2 days later than the controls, however, all 10 seeds did germinate. The transgenics were yellowish-pink when they first emerged but greened up in one to two days. At the emergence of the first true leaf, no difference in color was observed. Plants germinated from both the transgenic and control seeds developed normally.

E. Fatty Acid Analysis

Fatty acid composition of mature seeds was determined by GC analysis of single T2 seeds harvested from trangenic plants 3390-1 and 3390-8. Single seeds from both Random (R) and Maroon (M) populations (as defined above) were analyzed and compared to seeds from a 212186 control (SP001–1). The results of these analyses are provided in Table 3 below as weight % total fatty acids.

TABLE 3

FATTY ACID COMPOSITION OF 3390-1 AND 3390-8 LINES

| SAMPLE | 10:0 | 12:0 | 14:0 | 16:0 | 16:1 | 18:0 | 18:1 | 18:2 | 18:3 | 20:0 | 20:1 | 20:2 | 22:0 |
|---|---|---|---|---|---|---|---|---|---|---|---|---|---|
| CONTROL | 1.5 | 0 | 0.1 | 5.1 | 0.4 | 1.7 | 59.9 | 17.1 | 12.0 | 0.6 | 1.2 | 0.1 | 0.3 |
| CONTROL | 1.8 | 0 | 0.1 | 5.1 | 0.4 | 1.7 | 60.1 | 16.6 | 12.1 | 0.6 | 1.2 | 0.1 | 0.3 |
| CONTROL | 2.0 | 0 | 0.1 | 5.0 | 0.4 | 1.6 | 60.5 | 16.2 | 12.0 | 0.6 | 1.2 | 0.1 | 0.3 |
| CONTROL | 2.2 | 0 | 0.1 | 5.2 | 0.4 | 1.6 | 57.2 | 18.2 | 12.7 | 0.6 | 1.3 | 0.1 | 0.4 |
| CONTROL | 1.6 | 0 | 0.1 | 4.7 | 0.4 | 1.8 | 62.7 | 15.3 | 11.3 | 0.6 | 1.2 | 0.1 | 0.3 |
| 3390-1-R | 2.8 | 0 | 0.1 | 4.8 | 0.5 | 3.6 | 69.9 | 10.6 | 4.8 | 1.2 | 1.1 | 0.0 | 0.6 |
| 3390-1-R* | 1.5 | 0 | 0.1 | 4.7 | 0.3 | 1.5 | 58.1 | 19.3 | 12.3 | 0.5 | 1.2 | 0.1 | 0.3 |
| 3390-1-R | 3.5 | 0 | 0.1 | 4.2 | 0.3 | 2.6 | 71.1 | 9.6 | 5.8 | 1.0 | 1.2 | 0.0 | 0.6 |
| 3390-1-R* | 1.5 | 0 | 0.1 | 4.7 | 0.3 | 1.9 | 61.0 | 17.8 | 10.4 | 0.7 | 1.3 | 0.1 | 0.3 |
| 3390-1-R | 2.2 | 0 | 0.1 | 4.4 | 0.3 | 3.1 | 73.6 | 8.9 | 4.4 | 1.2 | 1.1 | 0.0 | 0.7 |
| 3390-1-R | 1.9 | 0 | 0.1 | 4.5 | 0.3 | 2.4 | 72.7 | 10.6 | 4.7 | 0.9 | 1.3 | 0.1 | 0.6 |
| 3390-1-R | 2.5 | 0 | 0.1 | 4.2 | 0.3 | 3.4 | 71.7 | 10.0 | 5.1 | 1.1 | 1.0 | 0.0 | 0.6 |
| 3390-1-R | 1.7 | 0 | 0.1 | 4.4 | 0.3 | 2.6 | 73.5 | 10.0 | 4.5 | 1.0 | 1.2 | 0.1 | 0.6 |
| 3390-1-R | 1.9 | 0 | 0.1 | 4.2 | 0.3 | 2.3 | 72.4 | 9.9 | 6.3 | 0.9 | 1.2 | 0.1 | 0.5 |
| 3390-1-R | 2.5 | 0 | 0.1 | 4.2 | 0.3 | 2.7 | 72.0 | 10.1 | 5.1 | 1.0 | 1.2 | 0.1 | 0.6 |
| 3390-1-R* | 1.5 | 0 | 0.1 | 4.7 | 0.3 | 1.7 | 58.5 | 18.5 | 12.6 | 0.6 | 1.2 | 0.1 | 0.3 |
| 3390-1-R | 2.8 | 0 | 0.1 | 4.6 | 0.4 | 3.7 | 71.8 | 9.1 | 4.2 | 1.3 | 1.2 | 0.0 | 0.7 |
| 3390-1-R | 1.8 | 0 | 0.1 | 4.0 | 0.3 | 2.3 | 72.4 | 11.1 | 5.2 | 0.9 | 1.3 | 0.1 | 0.5 |
| 3390-1-R | 1.7 | 0 | 0.1 | 4.4 | 0.3 | 2.7 | 73.9 | 9.9 | 4.2 | 1.0 | 1.2 | 0.1 | 0.6 |
| 3390-1-R | 1.7 | 0 | 0.1 | 4.6 | 0.4 | 2.6 | 71.4 | 10.9 | 5.5 | 1.0 | 1.3 | 0.1 | 0.6 |
| 3390-1-R | 2.7 | 0 | 0.1 | 4.2 | 0.3 | 2.8 | 72.1 | 9.9 | 5.0 | 1.1 | 1.3 | 0.0 | 0.6 |
| 3390-1-R | 2.0 | 0 | 0.1 | 4.5 | 0.3 | 3.0 | 72.5 | 9.7 | 4.6 | 1.2 | 1.3 | 0.1 | 0.7 |
| 3390-1-R | 1.8 | 0 | 0.1 | 4.9 | 0.4 | 3.4 | 71.8 | 10.4 | 4.2 | 1.2 | 1.2 | 0.0 | 0.7 |
| 3390-1-R* | 0.9 | 0 | 0.1 | 4.5 | 0.3 | 1.7 | 55.9 | 18.8 | 15.6 | 0.5 | 1.3 | 0.1 | 0.3 |
| 3390-1-R* | 1.4 | 0 | 0.1 | 4.8 | 0.4 | 1.7 | 57.1 | 18.0 | 14.4 | 0.6 | 1.2 | 0.1 | 0.3 |
| 3390-1-R* | 1.4 | 0 | 0.1 | 4.5 | 0.3 | 1.7 | 57.8 | 18.5 | 13.5 | 0.6 | 1.3 | 0.1 | 0.3 |
| 3390-1-R | 2.2 | 0 | 0.1 | 4.5 | 0.3 | 2.5 | 73.4 | 9.7 | 4.6 | 0.9 | 1.2 | 0.0 | 0.5 |
| 3390-1-R | 1.5 | 0 | 0.1 | 3.8 | 0.3 | 2.7 | 75.9 | 8.1 | 4.6 | 1.0 | 1.4 | 0.0 | 0.6 |
| 3390-1-R | 1.6 | 0 | 0.1 | 4.5 | 0.3 | 2.6 | 71.9 | 10.6 | 5.5 | 1.0 | 1.3 | 0.1 | 0.6 |
| 3390-1-R* | 1.3 | 0 | 0.1 | 6.2 | 0.5 | 1.4 | 53.6 | 21.7 | 13.2 | 0.5 | 1.1 | 0.1 | 0.3 |
| 3390-1-R | 2.1 | 0 | 0.1 | 4.3 | 0.3 | 2.4 | 72.3 | 10.7 | 5.1 | 0.9 | 1.2 | 0.0 | 0.6 |
| 3390-1-R* | 1.3 | 0 | 0.1 | 5.0 | 0.3 | 1.6 | 57.8 | 18.8 | 13.0 | 0.5 | 1.3 | 0.1 | 0.3 |
| 3390-1-R | 2.1 | 0 | 0.1 | 4.4 | 0.3 | 3.3 | 72.7 | 9.2 | 4.8 | 1.2 | 1.2 | 0.0 | 0.7 |
| 3390-1-R | 1.5 | 0 | 0.1 | 4.5 | 0.3 | 3.3 | 72.6 | 10.1 | 4.6 | 1.2 | 1.1 | 0.1 | 0.7 |
| 3390-1-R* | 1.2 | 0 | 0.1 | 4.7 | 0.3 | 1.9 | 59.9 | 17.1 | 12.6 | 0.6 | 1.3 | 0.1 | 0.4 |
| 3390-1-M | 2.8 | 0 | 0.1 | 4.0 | 0.3 | 2.8 | 69.8 | 10.6 | 7.1 | 0.9 | 1.2 | 0.0 | 0.4 |
| 3390-1-M | 2.0 | 0 | 0.1 | 4.9 | 0.4 | 3.3 | 70.3 | 11.1 | 4.9 | 1.2 | 1.2 | 0.1 | 0.7 |
| 3390-1-M | 1.5 | 0 | 0.1 | 4.4 | 0.3 | 3.2 | 73.4 | 9.5 | 4.3 | 1.3 | 1.3 | 0.0 | 0.8 |
| 3390-1-M | 1.5 | 0 | 0.1 | 4.5 | 0.3 | 2.8 | 72.7 | 10.0 | 5.1 | 1.1 | 1.3 | 0.0 | 0.7 |
| 3390-1-M | 1.8 | 0 | 0.1 | 4.2 | 0.3 | 3.1 | 73.5 | 9.6 | 4.7 | 1.1 | 1.2 | 0.0 | 0.6 |
| 3390-1-M | 1.5 | 0 | 0.1 | 4.7 | 0.3 | 2.9 | 71.6 | 10.7 | 5.1 | 1.1 | 1.2 | 0.1 | 0.7 |
| 3390-1-M | 1.5 | 0 | 0.1 | 4.5 | 0.3 | 3.2 | 72.6 | 10.2 | 4.3 | 1.2 | 1.3 | 0.0 | 0.8 |
| 3390-1-M | 1.8 | 0 | 0.1 | 4.4 | 0.3 | 2.9 | 72.0 | 10.4 | 5.2 | 1.1 | 1.2 | 0.1 | 0.6 |
| 3390-1-M | 1.5 | 0 | 0.1 | 4.4 | 0.3 | 2.6 | 73.6 | 10.0 | 4.5 | 1.1 | 1.2 | 0.1 | 0.7 |
| 3390-1-M | 2.3 | 0 | 0.1 | 4.3 | 0.3 | 3.0 | 73.0 | 9.7 | 4.5 | 1.1 | 1.2 | 0.0 | 0.6 |

TABLE 3-continued

FATTY ACID COMPOSITION OF 3390-1 AND 3390-8 LINES

| SAMPLE | 10:0 | 12:0 | 14:0 | 16:0 | 16:1 | 18:0 | 18:1 | 18:2 | 18:3 | 20:0 | 20:1 | 20:2 | 22:0 |
|---|---|---|---|---|---|---|---|---|---|---|---|---|---|
| 3390-8-R* | 1.0 | 0 | 0.1 | 4.9 | 0.3 | 1.6 | 59.2 | 18.9 | 11.9 | 0.5 | 1.2 | 0.1 | 0.3 |
| 3390-8-R | 2.1 | 0 | 0.1 | 4.2 | 0.3 | 2.7 | 71.9 | 10.2 | 5.6 | 1.0 | 1.2 | 0.1 | 0.6 |
| 3390-8-R | 1.5 | 0 | 0.1 | 4.4 | 0.3 | 2.3 | 72.5 | 10.4 | 5.7 | 0.9 | 1.4 | 0.1 | 0.6 |
| 3390-8-R* | 1.2 | 0 | 0.1 | 4.9 | 0.3 | 1.7 | 59.7 | 18.2 | 11.6 | 0.6 | 1.3 | 0.1 | 0.4 |
| 3390-8-R* | 1.5 | 0 | 0.1 | 4.7 | 0.3 | 1.6 | 58.7 | 18.5 | 12.2 | 0.6 | 1.3 | 0.1 | 0.4 |
| 3390-8-R | 1.8 | 0 | 0.1 | 4.2 | 0.3 | 2.9 | 73.4 | 9.2 | 5.2 | 1.1 | 1.3 | 0.0 | 0.6 |
| 3390-8-R* | 1.1 | 0 | 0.1 | 4.7 | 0.3 | 1.5 | 56.9 | 19.3 | 14.1 | 0.5 | 1.1 | 0.1 | 0.2 |
| 3390-8-R | 2.2 | 0 | 0.1 | 4.6 | 0.3 | 3.0 | 71.4 | 10.0 | 5.2 | 1.1 | 1.2 | 0.1 | 0.7 |
| 3390-8-R | 1.7 | 0 | 0.1 | 4.6 | 0.4 | 2.4 | 72.5 | 11.0 | 4.8 | 0.9 | 1.3 | 0.1 | 0.5 |
| 3390-8-R | 2.4 | 0 | 0.1 | 4.7 | 0.3 | 2.9 | 74.0 | 8.4 | 4.0 | 1.1 | 1.2 | 0.0 | 0.7 |
| 3390-8-R | 1.9 | 0 | 0.1 | 4.6 | 0.4 | 3.0 | 72.7 | 9.7 | 4.8 | 1.0 | 1.2 | 0.0 | 0.6 |
| 3390-8-R | 2.0 | 0 | 0.1 | 4.4 | 0.3 | 2.8 | 73.2 | 9.7 | 4.5 | 1.0 | 1.3 | 0.0 | 0.6 |
| 3390-8-R | 1.5 | 0 | 0.1 | 4.3 | 0.3 | 2.6 | 71.8 | 10.7 | 5.8 | 1.0 | 1.3 | 0.1 | 0.6 |
| 3390-8-R | 1.5 | 0 | 0.1 | 4.4 | 0.3 | 2.7 | 72.6 | 10.5 | 4.9 | 1.0 | 1.3 | 0.1 | 0.6 |
| 3390-8-R | 2.0 | 0 | 0.1 | 4.9 | 0.4 | 3.3 | 71.1 | 10.4 | 4.9 | 1.1 | 1.1 | 0.1 | 0.6 |
| 3390-8-R | 2.1 | 0 | 0.0 | 4.5 | 0.4 | 3.6 | 73.0 | 8.8 | 4.3 | 1.3 | 1.2 | 0.0 | 0.7 |
| 3390-8-R | 2.2 | 0 | 0.1 | 5.1 | 0.4 | 2.9 | 67.6 | 12.3 | 6.5 | 1.1 | 1.2 | 0.1 | 0.7 |
| 3390-8-R | 1.8 | 0 | 0.1 | 4.2 | 0.3 | 2.6 | 73.5 | 9.9 | 4.8 | 1.0 | 1.3 | 0.1 | 0.6 |
| 3390-8-R | 1.7 | 0 | 0.1 | 4.7 | 0.3 | 3.0 | 72.5 | 9.9 | 4.6 | 1.2 | 1.3 | 0.1 | 0.7 |
| 3390-8-R | 1.7 | 0 | 0.1 | 4.6 | 0.4 | 2.8 | 73.7 | 9.5 | 4.1 | 1.1 | 1.3 | 0.1 | 0.7 |
| 3390-8-R | 1.5 | 0 | 0.1 | 4.5 | 0.3 | 3.0 | 74.7 | 8.5 | 4.2 | 1.2 | 1.2 | 0.0 | 0.7 |
| 3390-8-R | 1.5 | 0 | 0.1 | 4.4 | 0.4 | 1.9 | 70.0 | 11.8 | 7.2 | 0.8 | 1.4 | 0.1 | 0.5 |
| 3390-8-R | 1.7 | 0 | 0.1 | 4.4 | 0.3 | 2.5 | 71.8 | 11.1 | 5.2 | 1.0 | 1.3 | 0.1 | 0.6 |
| 3390-8-R | 1.4 | 0 | 0.1 | 4.5 | 0.4 | 2.8 | 73.3 | 9.7 | 4.9 | 1.1 | 1.2 | 0.1 | 0.6 |
| 3390-8-R | 1.5 | 0 | 0.1 | 4.8 | 0.4 | 3.0 | 72.6 | 10.6 | 4.1 | 1.1 | 1.2 | 0.1 | 0.7 |
| 3390-8-R* | 1.4 | 0 | 0.1 | 5.8 | 0.4 | 2.9 | 54.0 | 20.0 | 13.0 | 0.8 | 1.1 | 0.1 | 0.4 |
| 3390-8-R | 1.4 | 0 | 0.1 | 4.4 | 0.3 | 2.7 | 71.2 | 10.8 | 6.0 | 1.0 | 1.3 | 0.1 | 0.6 |
| 3390-8-R | 1.7 | 0 | 0.1 | 4.6 | 0.4 | 2.8 | 72.6 | 10.0 | 5.1 | 1.0 | 1.2 | 0.1 | 0.6 |
| 3390-8-R* | 1.0 | 0 | 0.1 | 4.6 | 0.3 | 1.6 | 59.6 | 18.5 | 12.3 | 0.5 | 1.2 | 0.1 | 0.3 |
| 3390-8-R* | 1.1 | 0 | 0.1 | 4.6 | 0.3 | 1.4 | 56.5 | 20.4 | 13.4 | 0.5 | 1.3 | 0.1 | 0.3 |
| 3390-8-M | 1.8 | 0 | 0.1 | 4.7 | 0.4 | 3.3 | 70.1 | 11.1 | 5.5 | 1.2 | 1.1 | 0.1 | 0.7 |
| 3390-8-M | 1.5 | 0 | 0.1 | 4.3 | 0.3 | 3.0 | 73.0 | 10.3 | 4.3 | 1.1 | 1.2 | 0.1 | 0.7 |
| 3390-8-M | 1.9 | 0 | 0.1 | 4.5 | 0.4 | 3.7 | 73.1 | 8.9 | 4.2 | 1.3 | 1.2 | 0.0 | 0.7 |
| 3390-8-M | 1.6 | 0 | 0.1 | 4.4 | 0.3 | 2.5 | 73.4 | 9.7 | 5.1 | 1.0 | 1.3 | 0.1 | 0.7 |
| 3390-8-M | 1.3 | 0 | 0.1 | 4.4 | 0.3 | 3.0 | 73.7 | 9.6 | 4.4 | 1.1 | 1.3 | 0.0 | 0.7 |
| 3390-8-M | 2.1 | 0 | 0.1 | 4.3 | 0.3 | 3.2 | 74.0 | 8.9 | 4.1 | 1.2 | 1.2 | 0.1 | 0.6 |
| 3390-8-M | 2.1 | 0 | 0.1 | 3.9 | 0.3 | 1.6 | 71.6 | 11.9 | 5.7 | 0.7 | 1.5 | 0.1 | 0.5 |
| 3390-8-M | 1.6 | 0 | 0.1 | 4.6 | 0.3 | 2.8 | 71.0 | 11.8 | 4.8 | 1.0 | 1.3 | 0.1 | 0.6 |
| 3390-8-M | 2.1 | 0 | 0.1 | 4.8 | 0.4 | 3.2 | 70.3 | 10.7 | 5.2 | 1.2 | 1.2 | 0.1 | 0.7 |
| 3390-8-M | 1.6 | 0 | 0.1 | 4.5 | 0.3 | 2.9 | 72.7 | 9.9 | 4.8 | 1.1 | 1.3 | 0.0 | 0.7 |

The above data demonstrate a substantial increase in oleic acid (18:1) in seeds from each of the transgenic lines. The increase in oleic acid is at the expense of linoleic and linolenic acids, both of which were decreased in the transgenic lines. Increases in 18:0 and 20:0 fatty acids were also observed. Based on these data, the null seeds present in the Random population can be identified, and are marked on Table 3 with an asterisk (*). All of the seeds in the Maroon populations from each transgenic line have the observed altered fatty acid compostion, confirming that the altered fatty acid composition is the result of expression of the crtB gene.

Figure 5:
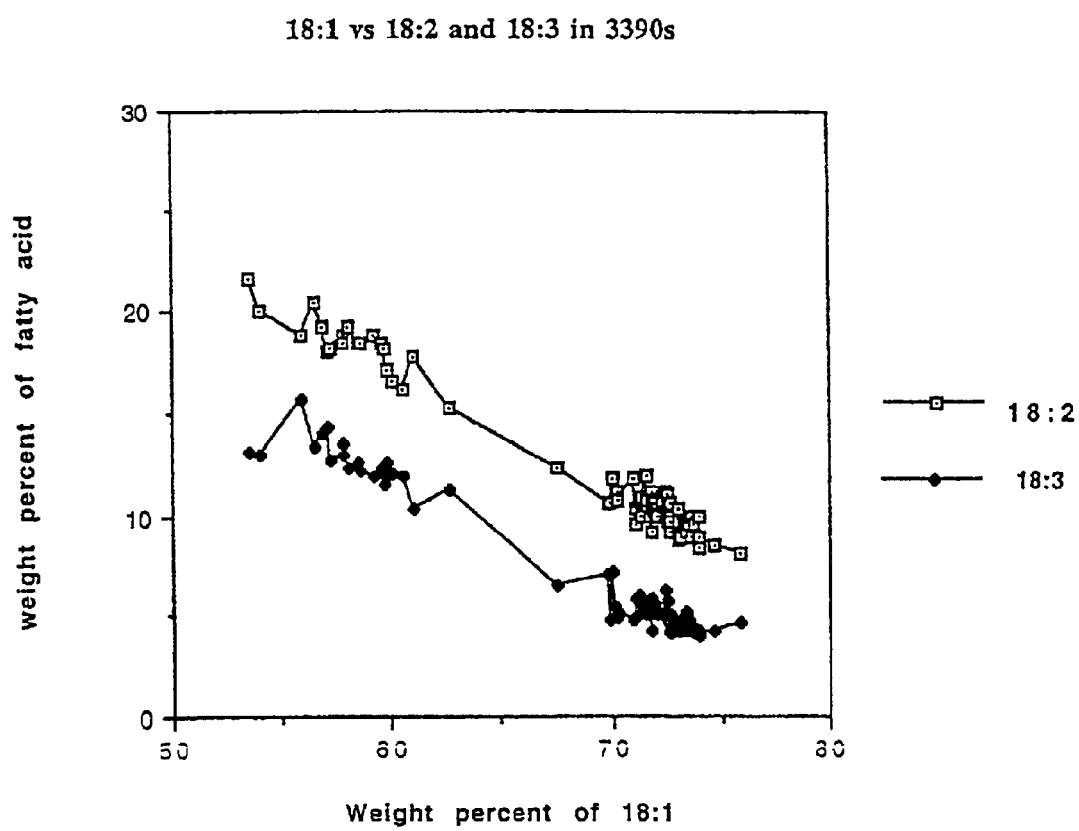
FIG. 5 shows a graph of the fatty acid analysis in pCGN3390 transformed seeds and demonstrates that the increase in 18:1 fatty acids correlates with a decrease in 18:2 and 18:3.
Figure 6:
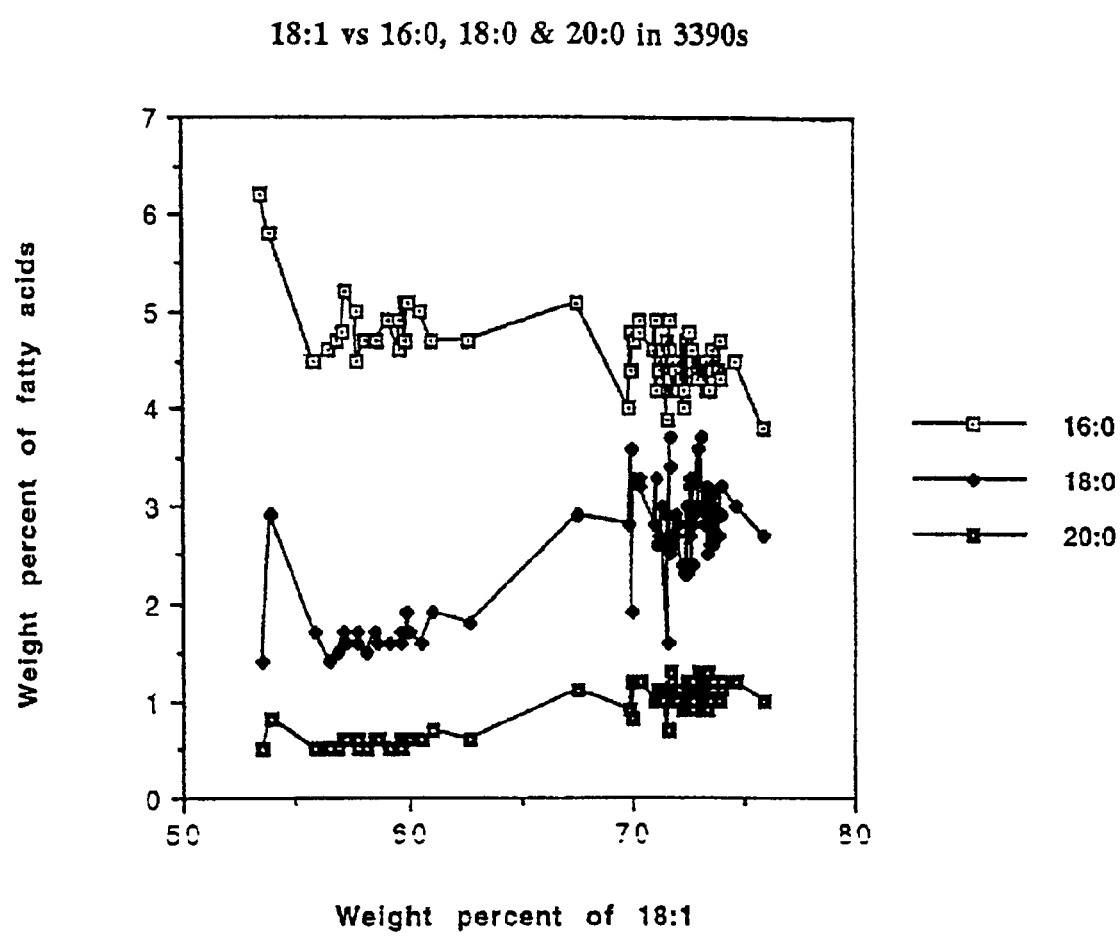
FIG. 6 shows a graph of the fatty acid analysis in pCGN3390 transformed seeds and demonstrates that the increase in 18:1 correlates with an increase in both 18:2 and 20:0, but little effect is seen in 16:0.
Figure 7:
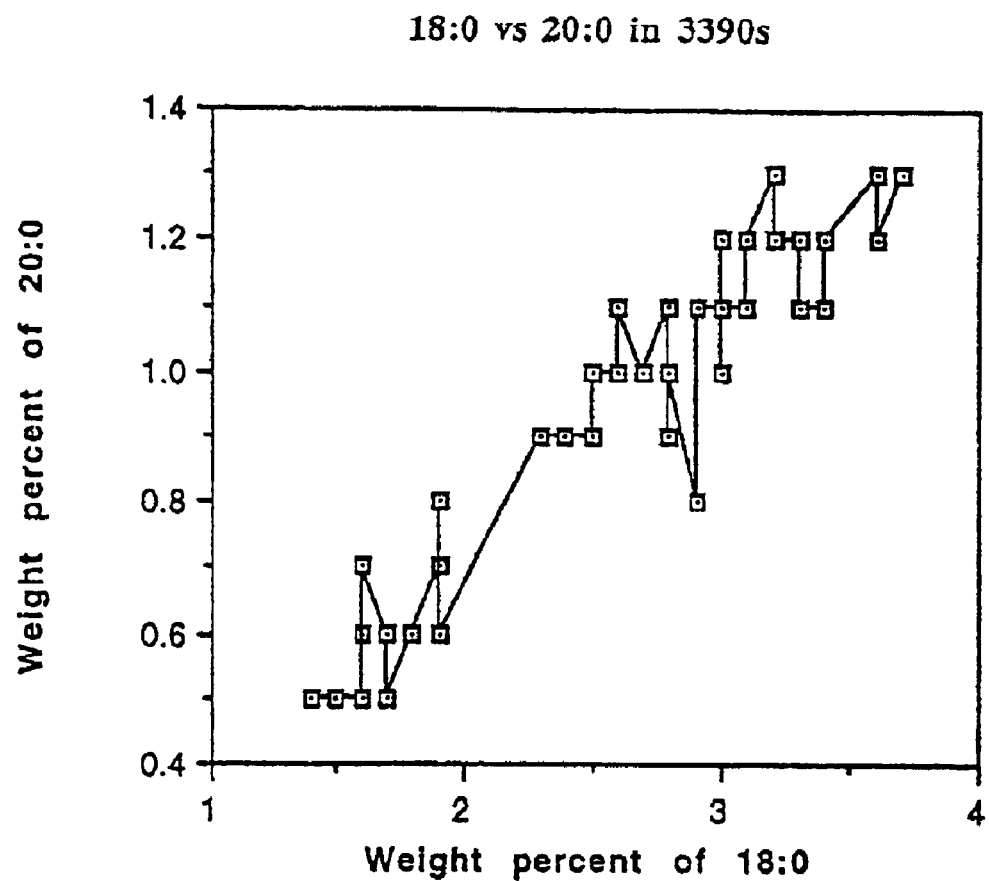
FIG. 7 shows a graph of the fatty acid analysis in pCGN3390 transformed seeds and demonstrates the increase in 18:0 correlates well with an increase in 20:0.
Figure 8:
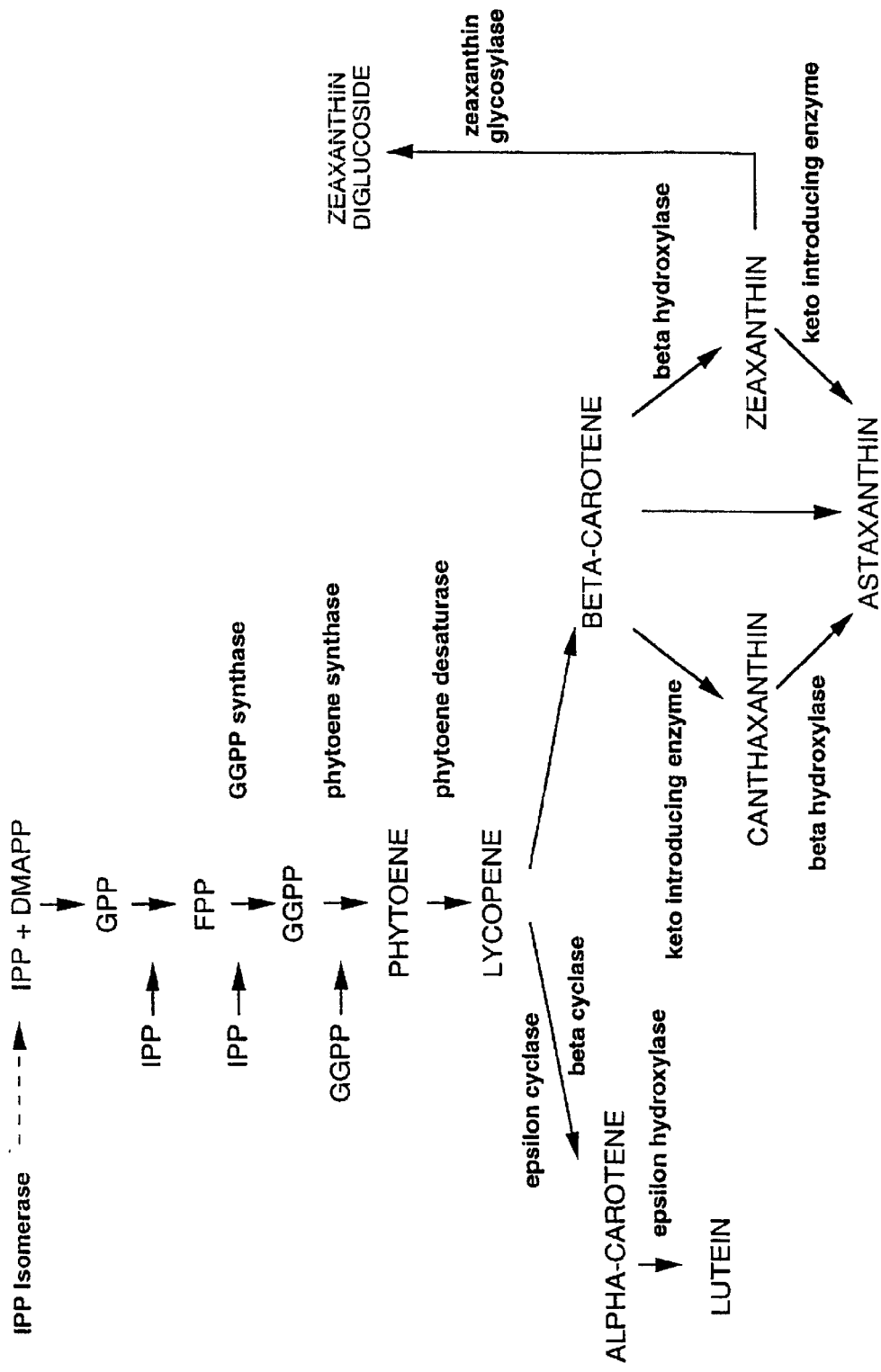
FIG. 8 shows a carotenoid biosynthesis pathway.

The trends in fatty acid composition data in the transgenic seeds which indicate positive and negative correlations of fatty acid composition changes with the observed increase in 18:1 levels are provided in FIGS. 5–7. The increase in 18:1 correlates with the decreases in 18:2 and 18:3. (FIG. 5). The increase in 18:1 also correlates with an increase in both 18:0 and 20:0, but little effect on 16:0 was seen (FIG. 6). The increase in 18:0 also correlated with an increase in 20:0 (FIG. 7).

F. Carotenoid Analysis of Mature Seeds from crtE Transgenic Plants

Carotenoids were analyzed in mature T2 seeds of 3392 B. napus plants tranformed to express the E. uredovora crtE gene. An approximately two fold increase in levels of lutein and β-carotene was observed in seeds of plant 3392-SP30021-16. Lycopene was also detected in these seeds and is undetectable in seeds of untransformed control plants. Analysis of seeds from 7 additional 3392 transformants did not reveal significant increases in the carotenoid levels.

EXAMPLE 3

Crosses of crtB Plants

A. Transgenic Oil Traits

To evaluate the high oleic trait of the napin-crtB transgenic plants in conjunction with expression of other oils traits, crosses off 3390-1-6-8 with a mangosteen thioesterase (5266) and a nutmeg thioesterase (3854; see WO 96/23892) were made. Crosses were also made with two low linoleic (LPOO4 and LP30108) varieties. Half-seed analyses of carotenoids and fatty acid composition were conducted on the segregating seeds, and the average of the half seed values are shown below in Tables 4 and 5.

TABLE 4

Carotenoid Levels in Half Seeds Resulting from 3390 Crosses

| Cross | Lutein | Lycopene | α-Carotene | β-Carotene | Total |
| --- | --- | --- | --- | --- | --- |
| F1 3390-SP001-1-6-8 × SP30021 | 21.6 | 26.2 | 271.5 | 413.1 | 732.4 |
| F1 3390-SP001-1-6-8 × 5266-SP30021-5-26 | 18.0 | 21.7 | 187.9 | 284.1 | 511.7 |
| F1 3390-SP001-1-6-8 × 5266-SP30021-35-2 | 16.2 | 22.1 | 223.0 | 318.4 | 579.7 |
| F1 3390-SP001-1-6-8 × 5266-SP30021-35-12 | 19.5 | 22.9 | 196.8 | 312.8 | 552.0 |
| F1 3390-SP001-1-6-8 × LP30108-19 | 23.7 | 22.7 | 213.4 | 355.0 | 614.8 |
| F1 LP30108-19 × F1 3390-SP001-1-6-8 | 16.4 | 19.6 | 156.7 | 224.5 | 417.2 |

TABLE 5

Fatty Acid Composition in Half Seeds Resulting from 3390 Crosses

| STRAIN_ID | %14:0 | %16:0 | %18:0 | %18:1 | %18:2 | %18:3 | %20:0 |
| --- | --- | --- | --- | --- | --- | --- | --- |
| (3390-SP001-1-6-8 X SP30021) | 0.05 | 3.55 | 1.70 | 74.78 | 11.29 | 5.71 | 0.73 |
| (3390-SP001-1-6-8 X 5266-SP30021-35-12) | 0.06 | 3.84 | 11.37 | 62.86 | 11.06 | 5.08 | 3.38 |
| (3390-SP001-1-6-8 X 5266-SP30021-35-2) | 0.06 | 3.68 | 11.27 | 64.80 | 9.81 | 5.16 | 3.04 |
| 3390-SPOO1-1-6-8 X 5266-SP30021-5-26 | 0.06 | 3.66 | 15.36 | 60.78 | 9.30 | 4.77 | 3.87 |
| (3390-SP001-1-6-1 X 3854-SP30021-20-3) | 2.69 | 9.80 | 3.65 | 64.62 | 9.72 | 4.57 | 1.51 |
| (3390-SP001-1-6-1 X 3854-SP30021-20-1) | 6.14 | 16.35 | 5.12 | 54.91 | 8.23 | 4.23 | 2.03 |
| (3390-SP001-1-6-1 X 5266-LP004-2-31) | 0.07 | 3.82 | 11.67 | 64.52 | 11.46 | 3.14 | 3.08 |
| (3390-SP001-1-6-8 X LP30108-19) | 0.05 | 3.80 | 1.44 | 73.66 | 14.02 | 3.93 | 0.67 |
| (LP30108-19 X 3390-SP001-1-6-8) | 0.04 | 3.31 | 1.79 | 79.69 | 9.26 | 2.97 | 0.75 |
| SP001-4-10 | 0.07 | 4.44 | 0.99 | 56.06 | 21.79 | 14.31 | 0.44 |
| 3390-SPOO1-1-6-8 | 0.04 | 3.46 | 1.44 | 77.26 | 9.30 | 5.71 | 0.63 |

As the above results demonstrate, a dramatic increase (100 to 200 fold) in α- and β-carotene as well as a 60 fold increase in total carotenoids may be obtained by transformation of plants for expression of an early carotenoid biosynthesis gene under the regulatory control of promoter preferentially expressed in plant seed tissue. This increase in flux primes the pathway for the production of speciality products as described above, and also results in increased production of α-tocopherol (Vitamin E).

Furthermore, it is evident that the fatty acid composition can also be altered in the transgenic plant seeds. In this manner, seeds can be used to produce novel products, to provide for production of particular carotenoids, to provide high oleic oils, and the like.

All publications and patent applications mentioned in the specification are indicative of the level of skill of those skilled in the art to which this invention pertains. AU publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A transgenic *Brassica* plant that produces seed having an increased total carotenoid level, wherein said transgenic *Brassica* plant contains a DNA coding sequence of a crtB gene comprising SEQ ID NO: 1 and wherein said increased total carotenoid level is at least about 10 fold over native total carotenoid levels in said seed.

2. The transgenic *Brassica* plant according to claim 1, wherein said seed produces an increased level of at least one carotenoid compound selected from the group consisting of phytoene, lycopene, α-carotene, β-carotene, α-cryptoxanthin, and phytofluene, wherein the level is increased at least about 100 fold over native levels in said seed.

3. The transgenic *Brassica* plant according to claim 2, wherein said seed produces an increased level of at least one carotenoid compound selected from the group consisting of β-carotene and β-carotene.

4. The transgenic *Brassica* plant according to claim 1, wherein said DNA coding sequence of a crtB gene comprising SEQ ID NO: 1 is operably linked to a transcriptional initiation region from a gene preferentially expressed in *Brassica* seed tissue.

5. The transgenic *Brassica* plant according to claim 4, wherein said transcriptional initiation region is from a napin gene.

6. The transgenic *Brassica* plant according to claim 1, wherein said increase in total carotenoid level is about 25 fold.

7. The transgenic *Brassica* plant according to claim 1, wherein said increase in total carotenoid level is about 60 fold.

8. The transgenic *Brassica* plant according to claim 1, wherein said increase in total carotenoid level is about 100 fold.

9. A transformed *Brassica* seed containing a DNA coding sequence of a crtB gene comprising SEQ ID NO: 1, wherein said transformed seed has an increased level of at least one carotenoid compound selected from the group consisting of phytoene, lycopene, α-carotene, β-carotene, α-cryptoxanthin, and phytofluene, wherein said increased level is at least about 100 fold over native levels in said seed.

10. The transformed *Brassica* seed according to claim 9, wherein said seed produces increased levels of phytoene, lycopene, α-carotene, β-carotene, α-cryptoxanthin, and phytofluene.

11. The transformed *Brassica* seed according to claim 9, wherein said seed produces increased levels of α-carotene and β-carotene.

12. The transformed *Brassica* seed according to claim 9, wherein said DNA coding sequence of a crtB gene comprising SEQ ID NO: 1 is operably linked to a transcriptional initiation region from a gene preferentially expressed in *Brassica* seed tissue.

13. The transformed *Brassica* seed according to claim 12, wherein said transcriptional initiation region is from a napin gene.

14. A transgenic *Brassica* plant that produces a seed having an increased carotenoid level, wherein said transgenic *Brassica* plant contains a construct comprising a transcriptional initiation region from a gene preferentially expressed in a plant seed, a DNA coding sequence of a crtB gene comprising SEQ ID NO: 1, and a transcriptional termination region, and wherein said seed exhibits an increased level of at least one carotenoid compound selected from the group consisting of phytoene, lycopene, α-carotene, β-carotene, α-cryptoxanthin, and phytofluene, wherein said increased level is at least about 100 fold over native levels in said seed.

15. The transgenic *Brassica* plant of claim 14, wherein said seed produces increased levels of phytoene, lycopene, α-carotene, β-carotene, α-cryptoxanthin, and phytofluene.

16. The transgenic *Brassica* plant of claim 14, wherein said seed produces an increased level of at least one carotenoid compound selected from the group consisting of α-carotene and β-carotene.

17. The transgenic *Brassica* plant according to claim 14, wherein said transcriptional initiation region is from a gene preferentially expressed in *Brassica* seed tissue.

18. The transgenic *Brassica* plant according to claim 14, wherein said transcriptional initiation region is from a napin gene.

19. A transformed *Brassica* seed containing a construct comprising a transcriptional initiation region from a gene preferentially expressed in a plant seed, a DNA coding sequence of a crtB gene comprising SEQ ID NO: 1, and a transcriptional termination region, and wherein said transformed seed exhibits an increased level of at least one carotenoid compound selected from the group consisting of phytoene, lycopene, α-carotene, β-carotene, α-cryptoxanthin, and phytofluene, wherein said increased level is at least about 100 fold over native levels in said seed.

20. The transformed *Brassica* seed of claim 19, wherein said seed produces increased levels of phytoene, lycopene, α-carotene, β-carotene, α-cryptoxanthin, and phytofluene.

21. The transformed *Brassica* seed according to claim 19, wherein said seed produces increased levels of α-carotene and β-carotene.

22. The transformed *Brassica* seed according to claim 19, wherein said transcriptional initiation region is from a gene preferentially expressed in *Brassica* seed tissue.

23. The transformed *Brassica* seed according to claim 19, wherein said transcriptional initiation region is from a napin gene.

24. A transgenic *Brassica* plant that produces seed having an increased level of at least one carotenoid compound selected from the group consisting of phytoene, lycopene, α-carotene, β-carotene, α-cryptoxanthin, and phytofluene, wherein said increased level is at least about 100 fold over native levels in said seed, wherein said transgenic *Brassica* plant contains a DNA coding sequence of a crtB gene comprising SEQ ID NO: 1.

25. The transgenic *Brassica* plant according to claim 24, wherein said seed produces increased levels of phytoene, lycopene, α-carotene, β-carotene, α-cryptoxanthin, and phytofluene.

26. The transgenic *Brassica* plant according to claim 24, wherein said seed produces increased levels of α-carotene and β-carotene.

27. The transgenic *Brassica* plant according to claim 24, wherein said DNA coding sequence of a crtB gene comprising SEQ ID NO: 1 is operably linked to a transcriptional initiation region from a gene preferentially expressed in *Brassica* seed tissue.

28. The transgenic *Brassica* plant according to claim 27, wherein said transcriptional initiation region is from a napin gene.

29. The transgenic *Brassica* plant according to claim 2, wherein said seed produces increased levels of phytoene, lycopene, α-carotene, β-carotene, α-cryptoxanthin, and phytofluene.

* * * * *

UNITED STATES PATENT AND TRADEMARK OFFICE
CERTIFICATE OF CORRECTION

PATENT NO. : 6,972,351 B2
DATED : December 6, 2005
INVENTOR(S) : Christine Shewmaker Page 1 of 1

It is certified that error appears in the above-identified patent and that said Letters Patent is hereby corrected as shown below:

Column 27,
Line 47-50, should read:
-- 3. The trangenic *Brassica* plant according to claim 2, wherein said seed produces an increased level at least on e carotenoid compound selected from the group consisting of [β]α-carotene and β-cartene. --.

Signed and Sealed this

Twenty-third Day of May, 2006

JON W. DUDAS
*Director of the United States Patent and Trademark Office*